(12) United States Patent
Gellman et al.

(10) Patent No.: US 8,530,631 B2
(45) Date of Patent: Sep. 10, 2013

(54) SYNTHETIC AMPHIPHILES FOR MEMBRANE PROTEIN MANIPULATION

(75) Inventors: Samuel Helmer Gellman, Madison, WI (US); Pil Seok Chae, Madison, WI (US); Brian Kobilka, Palo Alto, CA (US); Soren Rasmussen, Palo Alto, CA (US)

(73) Assignees: Wisconsin Alumni Research Foundation, Madison, WI (US); The Board of Trustees of the Leland Stanford Junior University, Palo Alto, CA (US)

( * ) Notice: Subject to any disclaimer, the term of this patent is extended or adjusted under 35 U.S.C. 154(b) by 439 days.

(21) Appl. No.: 12/731,000

(22) Filed: Mar. 24, 2010

(65) Prior Publication Data

US 2010/0311956 A1    Dec. 9, 2010

Related U.S. Application Data

(60) Provisional application No. 61/162,963, filed on Mar. 24, 2009.

(51) Int. Cl.
*C07H 15/02* (2006.01)
*C07H 15/04* (2006.01)

(52) U.S. Cl.
USPC ............................. 536/4.1; 536/17.9

(58) Field of Classification Search
None
See application file for complete search history.

(56) References Cited

U.S. PATENT DOCUMENTS

| 6,172,262 | B1 | 1/2001 | Mc Quade et al. |
| 2009/0270598 | A1 | 10/2009 | Gellman et al. |
| 2010/0311956 | A1 | 12/2010 | Gellman et al. |

OTHER PUBLICATIONS

Chierici, S. et al., Chemistry and Physics of Lipids, "Synthesis and interfacial behavior of a gemini neoglycolipid", 1997, vol. 87, pp. 91-101.*

Dumoulin, F. et al., Chem. Eur. J., "Synthesis and Liquid Crystalline Properties of Mono-, Di- and Tri-O-alkyl Pentaerythritol Derivatives Bearing Tri-, Di- or Monogalactosyl Heads: The Effects of Curvature of Molecular Packing on Mesophase Formation", 2007, vol. 13, pp. 5585-5600.*
Prive, G. G. et al., Methods, "Detergents for the Stabilization and Crystallization of Membrane Proteins", 2007, vol. 41, pp. 388-397.*
Kim, Y. S. et al., Tetrahedron Letters, "Synthesis of New Building Blocks for Boron-Rich Oligomers in Boron Neutron Capture Therapy (BNCT). II. Monomers Derived From 2,2-Disubstituted-1,3-Diols", vol. 36, No. 29, pp. 5147-5150.*
Silverman, Richard B., The Organic Chemistry of Drug Design and Drug Action, Academic Press, copyright 1992, pp. 19-23.*
Chae, P. S., et al., "Glycotripod Amphiphiles for Solubilization and Stabilization of a Membrane-Protein Superassembly: Importance of Branching in the Hydrophillic Portion", *ChemBioChem*, 9, (2008), 1706-1709.
Hjelmeland, L. M., "The Design and Synthesis of Detergents for Membrane Biochemistry", *Methods in Enzymology*, 124, (1986), 135-164.
Chierici et al., "Synthesis and interfacial behaviour of a gemini neoglycolipid," Chemistry and Physics of Lipids (1997) 87: 91-101.
Dumoulin et al., "Synthesis and liquid crystalline properties of mono-, di- and tri-O-alkyl pentaerythritol derivatives bearing tri-, di-, or monogalactosyl heads: The effects of curvature of molecular packing on mesophase formation," Chem. Eur. J. (2007) 13: 5585-5600.
Prive, G., "Detergents for the stabilzation and crystallization of membrane proteins," Methods (2007) 41: 388-397.

* cited by examiner

*Primary Examiner* — Shaojia Anna Jiang
*Assistant Examiner* — Bahar Craigo
(74) *Attorney, Agent, or Firm* — Billion & Armitage; Michael H. Haukaas

(57) ABSTRACT

The invention provides amphiphilic compounds and methods for manipulating membrane proteins. Compounds of the invention, for example, the compounds of Formulas I-XIX, can be prepared from readily available starting materials. The amphiphilic compounds can manipulate membrane protein at relatively low concentrations compared to many known detergents. The compounds can be used to aid the isolation of membrane proteins, for example, to aid their solubilization and/or purification. The compounds can also be used to aid the functional and structural determination of membrane proteins, including their stabilization and crystallization.

6 Claims, 5 Drawing Sheets

SYNTHETIC AMPHIPHILES FOR MEMBRANE PROTEIN MANIPULATION

RELATED APPLICATIONS

This application claims priority under 35 U.S.C. §119(e) to U.S. Provisional Patent Application No. 61/162,963, filed Mar. 24, 2009, which is incorporated herein by reference.

GOVERNMENT SUPPORT

This invention was made with government support under GM075913 and NS028471 awarded by the National Institutes of Health. The government has certain rights in the invention.

BACKGROUND OF THE INVENTION

Isolation and physical characterization of membrane proteins remains a central challenge in biomolecular science. Isolating membrane proteins and obtaining their crystal structures is important to furthering an understanding of their function and role in metabolic pathways. The lack of sufficient methods for membrane protein isolation, purification, and crystallization represents a significant hindrance to fundamental and applied biological research because these proteins perform so many crucial functions in vivo. Membrane proteins are difficult to manipulate and ultimately crystallize because these macromolecules are rarely soluble in simple aqueous buffers.

Solubilizing membrane proteins for physical characterization and crystallization requires that the membrane protein be combined with a synthetic amphiphile, typically a detergent. The resulting crystal is generally a protein-detergent complex rather than the protein alone. The detergent therefore plays an important role in determining whether high quality crystals will form. High quality crystals are essential for structural determination and characterization, such as by X-ray crystallography.

Three-dimensional structure determination for membrane proteins has been successful only within the past two decades, and the set of known membrane protein structures is far smaller than the set of known soluble protein structures. Synthetic amphiphiles, such as detergents, are crucial tools in this field. They are used to extract embedded proteins from the membranes in which they naturally occur and to maintain native protein conformation in the solubilized state. Physical characterization is often carried out with protein-amphiphile complexes, and such complexes are usually the basis for crystallization efforts. Growth of high-quality crystals is typically the rate-limiting step in structure determination.

Although more than 120 detergents are commercially available, membrane protein manipulation is still challenging. Many membrane proteins tend to denature and aggregate in these commercially available detergents. Thus, it is of great interest to develop novel classes of amphiphiles with enhanced properties in terms of solubilization and stabilization to aid fundamental and applied protein research. Preferably, the amphiphiles could be synthesized from readily available starting material by convenient protocols. The practical aspects of such agents would significantly increase their utility.

SUMMARY

The invention provides new tools for membrane technology, including effective solubilizing agents and methods for solubilizing, isolating, and characterizing membrane proteins, including intrinsic membrane proteins. The solubilizing agents can include synthetic amphiphiles that exhibit favorable solubilization and stabilization properties in challenging biochemical systems such as, for example, lipid bilayers, photosynthetic superassemblies, and G protein-coupled receptors (GPCRs) such as the beta-2-adrenergic receptor. Accordingly, the invention also provides novel compounds, such as the carbohydrate-based solubilizing agents described herein, for use in manipulating membrane proteins. The novel solubilizing agents can be prepared from readily available starting materials.

Accordingly, the invention provides a compound of Formula I:

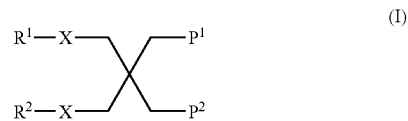

(I)

wherein $R^1$ is $(C_4$-$C_{20})$alkyl, $(C_4$-$C_{20})$cycloalkyl, $(C_3$-$C_{20})$cycloalkyl$(C_1$-$C_{20})$alkyl, $(C_6$-$C_{10})$aryl, $(C_6$-$C_{10})$aryl$(C_1$-$C_{20})$alkyl;

$R^2$ is $(C_4$-$C_{20})$alkyl, $(C_4$-$C_{20})$cycloalkyl, $(C_3$-$C_{20})$cycloalkyl$(C_1$-$C_{20})$alkyl, $(C_6$-$C_{10})$aryl, $(C_6$-$C_{10})$aryl$(C_1$-$C_{20})$alkyl;

each X is independently $CH_2$, O, S, —C(=O)NH—, or a direct bond;

$P^1$ is a monosaccharide, a disaccharide, —N($R^3$)-monosaccharide, —N($R^3$)-disaccharide, or —Y—($C_1$-$C_6$)alkyl-Z; $P^2$ is a monosaccharide, a disaccharide, —N($R^3$)-monosaccharide, —N($R^3$)-disaccharide, or —Y—($C_1$-$C_6$)alkyl-Z;

each Y is independently —C(=O)NH—, $CH_2$, or a direct bond;

each Z is independently —$N^+$($O^-$)(Me)$_2$, —OP(=O)($O^-$)—($C_1$-$C_6$)alkyl-$N^+$(($C_1$-$C_3$)alkyl)$_3$, —$N^+$(Me)$_2$-($C_1$-$C_6$)alkyl-$SO_3^-$, or —$N^+$(Me)$_2$-($C_1$-$C_6$)alkyl-$CO_2^-$; and $R^3$ is hydrogen or ($C_1$-$C_6$)alkyl optionally substituted with a hydroxy group.

The groups $R^1$ and $R^2$ are can be selected independently of each other. Accordingly, they can be the same or different. In one embodiment, $R^1$ and $R^2$ are each independently ($C_5$-$C_{16}$)alkyl, ($C_4$-$C_8$)cycloalkyl, phenyl($C_1$-$C_{12}$)alkyl, or ($C_3$-$C_{20}$)cycloalkyl($C_1$-$C_8$)alkyl.

In some embodiments, X is O, S, —C(=O)NH—.

In some embodiments, $P^1$ and $P^2$ are both monosaccharides. $P^1$ and $P^2$ can include glucose or mannose.

In some embodiments, $P^1$ and $P^2$ are both disaccharides. $P^1$ and $P^2$ can include maltose, galactose, or sucrose.

In some embodiments, at least one of groups $R^1$ and $R^2$ is $(C_6$-$C_{10})$aryl($C_1$-$C_{20}$)alkyl, and the $(C_6$-$C_{10})$aryl moiety is optionally substituted with one to five ($C_1$-$C_6$)alkyl, ($C_1$-$C_6$)alkoxy, nitro, halo, or trifluoromethyl groups.

In some embodiments, $P^1$ and $P^2$ are —N($R^3$)-monosaccharide or —N($R^3$)-disaccharide, and $R^3$ is hydrogen. In other embodiments, $P^1$ and $P^2$ are —N($R^3$)-monosaccharide or —N($R^3$)-disaccharide, and $R^3$ is methyl, ethyl, or 2-hydroxyethyl.

In some embodiments, $P^1$ and $P^2$ are —Y—($C_1$-$C_6$)alkyl-Z. For example, the compound can be a compound of any one of Formulas XII-XII described below. Accordingly, —($C_1$-$C_6$)alkyl- can be —$CH_2$—, —$CH_2CH_2$—, —$CH_2CH_2CH_2$—, —$CH_2CH_2CH_2$—$CH_2$—, —CH₂CH₂CH₂CH₂—CH₂—, or —CH₂CH₂CH₂CH₂CH₂CH₂—, or a branched variation thereof.

The invention also provides a compound of Formula I that is a compound of Formula II:

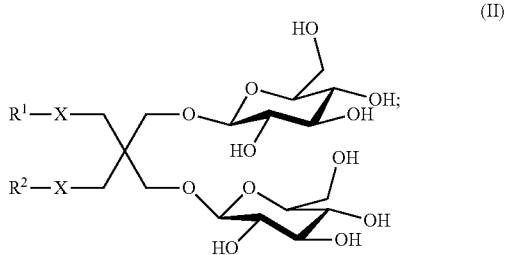

(II)

where R¹, R², and X are as defined for Formula I.

The invention further provides a compound of Formula I that is a compound of Formula III:

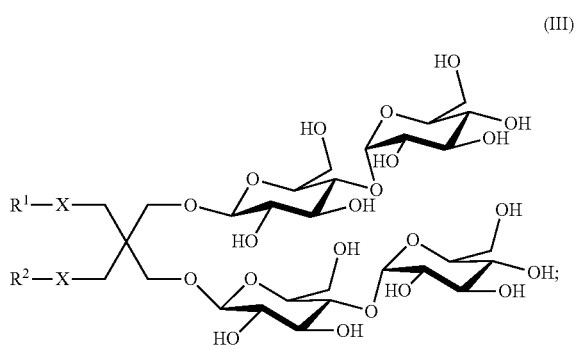

(III)

where R¹, R², and X are as defined for Formula I.

The invention yet further provides a compound of Formula I that is a compound of Formula IV or Formula V:

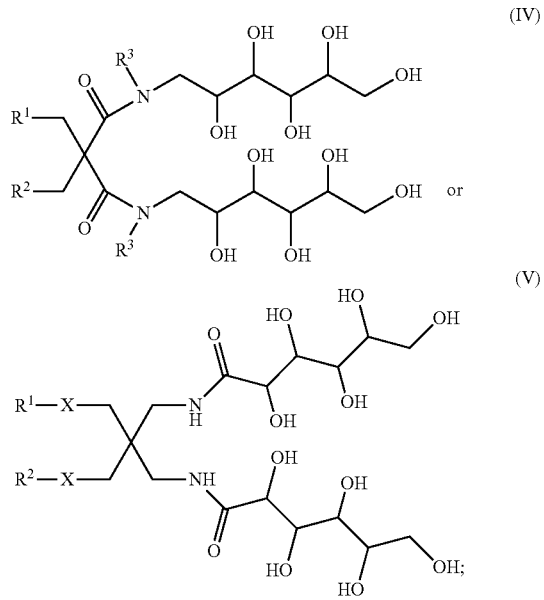

(IV)

(V)

where R¹, R², R³, and X are as defined for Formula I. Accordingly, in some embodiments, the carbon located between the quarternary carbon and P¹ and/or P² can be optionally substituted with an oxo group.

In some embodiments, R¹ and R² are each independently selected from pentyl, hexyl, heptyl, octyl, nonyl, decyl, undecyl, dodecyl, tridecyl, tetradecyl, pentadecyl, 4-tert-butylphenyl, cyclopentyl, cyclohexyl, 2-phenylethyl, 3-cyclohexylpropyl, 4-cyclohexylbutyl, norbornylmethyl, adamantly, dicyclohexylmethyl, 3,5-bis(trifluoromethyl)phenylmethyl, or 3,5-difluorophenylmethyl.

In some embodiments, the compound of the invention is a compound illustrated in Schemes E, F, or G.

The invention also provides compositions that include a plurality of an amphiphilic compound as described herein, e.g., a compound of any one of Formulas I-XIX, and a membrane protein.

The invention provides methods for manipulating membrane proteins. For example, a method is provided for solubilizing a membrane protein by contacting the protein in an aqueous environment with an effective amount of a compound as described herein (or by allowing the protein and the compound to suitably interact), and optionally heating the protein and the compound, to provide the solubilized protein encapsulated in micelles of the compound. The effective amount of the compound can be an amount of the compound necessary to achieve its critical micelle concentration, about 0.5-5 wt. %, about 1-2 wt. %, or to about ten times the amount of the compound necessary to achieve its critical micelle concentration. The method can also include employing a buffer, a second amphiphile or detergent, or other reagents, in the aqueous environment to aid in the solubilization and stabilization of membrane proteins.

The invention also provides a method of purifying a membrane protein by contacting the protein (or allowing the protein to interact) in an aqueous environment with an effective amount of a compound as described herein, to form micelles comprising a plurality of the compounds surrounding the protein, and isolating the micelles, to provide the purified membrane protein encapsulated in micelles of the compound. Other techniques for using the amphiphilic compounds described herein include techniques for stabilizing, crystallizing, and/or characterizing a protein while in a detergent micelle made up of a compound described herein.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

DETAILED DESCRIPTION

Figure 1:
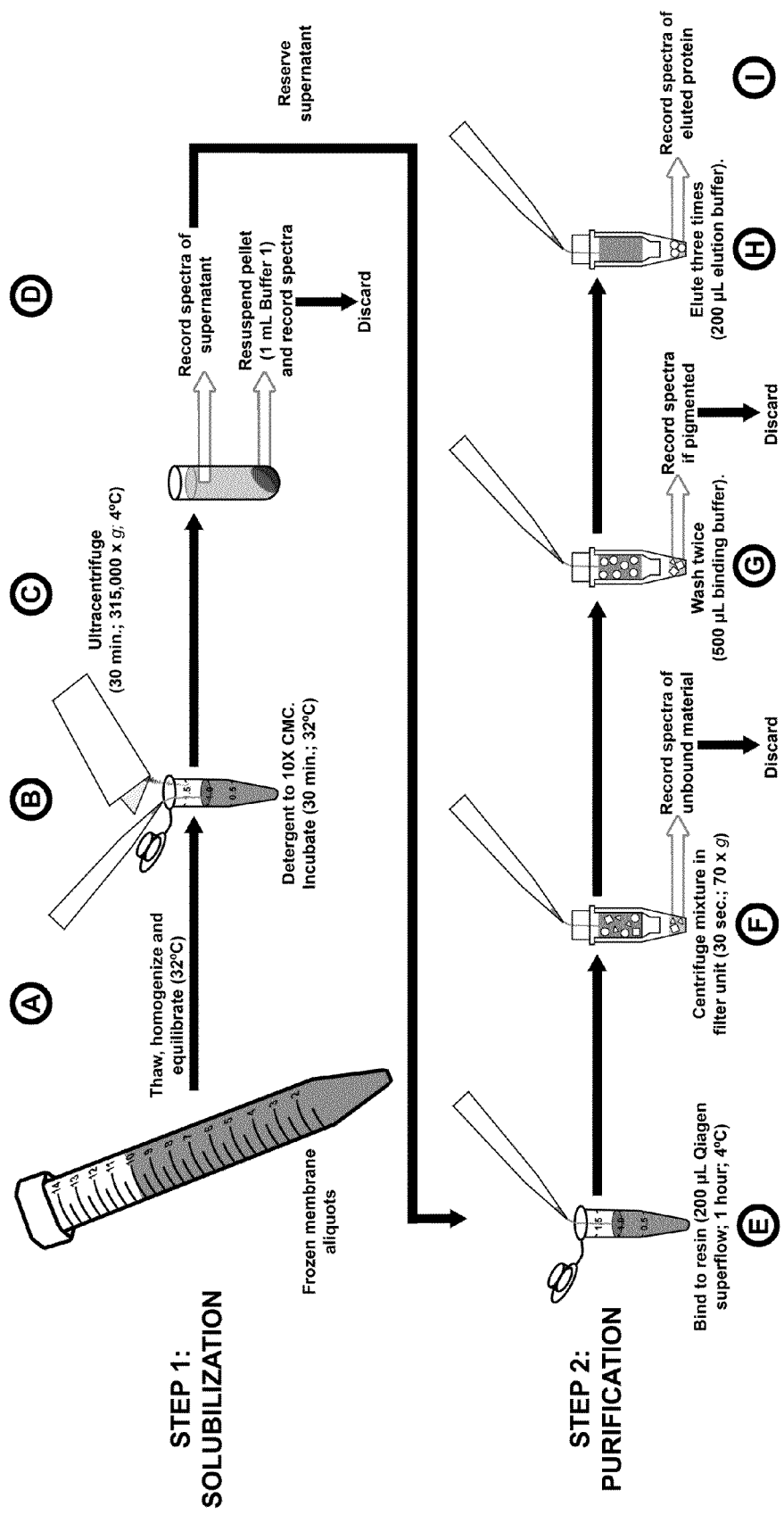
FIG. 1 illustrates solubilization and purification steps employed in the assay described in Example 2, according to an embodiment of the invention.

Many integral membrane proteins are not stable in the presence of detergents. Therefore, there is a need for new synthetic detergents that can maintain the native state of integral membrane proteins long enough for structural studies. Several non-classical amphiphiles have been reported for this purpose, however they amphiphiles were typically difficult to prepare in large quantities and thus far have not been shown to be compatible with the crystal growth of membrane proteins suitable for structural determination. The compounds described herein provide several tools to aid the achievement of these challenging goals. New amphiphiles disclosed herein are mild enough to maintain some membrane proteins stable, for example, for a longer period of time than DDM, which is one of the most effective detergents for membrane protein stabilization, or for at least about two weeks. The properties of these amphiphiles can be fine-tuned by employing a variety of the hydrophobic groups, for example, of different carbon lengths and structural arrangements, such as in branched alkyl groups, cycloalkyl groups, or aryl groups.

A variety of known biochemical detergents have been used in manipulating various types of membrane proteins, including decylmaltoside (DM), dodecylmaltoside (DDM), octyl glucoside (OG), nonylglucoside (NG), and lauryldimethylamine oxide (LDAO). Detergents such as LDAO and OG are considered to be rather harsh detergents. They form small compact micelles in solution. They have been used to crystallize some proteins; the crystallization process may have been aided by the formation of small sized protein-detergent complexes. However, they are not effective at maintaining the native state of many membrane proteins, which tend to denature and form irreversible aggregates.

DDM is considered a milder detergent than LDAO and OG. It has been found to be more effective at maintaining the native states of integral membrane proteins in solution. However, DDM forms relatively large micelles, resulting in large protein-detergent complexes. Large protein-detergent complexes can be problematic for obtaining effective results in NMR studies and crystallization trials.

Accordingly, new amphiphiles are sought that have more ideal properties for solubilization, isolation, purification, stabilization, crystallization, and/or structural determination of membrane proteins, including intrinsic membrane proteins. Such amphiphiles should form small micelles, which result in small membrane-protein complexes. The detergent strength of the amphiphiles should be relatively mild, thereby allowing for the maintenance of the native structure of membrane proteins with little or no denaturing. Additionally, the amphiphiles are preferably prepared from readily available starting materials, allowing for facile synthesis and widespread practical application. The amphiphiles described herein are provided to meet these needs.

The new detergents described herein have been evaluated with a R. capsulatus photosynthetic superassembly solubilization assay developed in collaboration with Argonne National Laboratory. The assay was previously used to evaluate numerous commercial detergents. The detergents described herein were found to be sufficiently mild such that they maintain several membrane proteins substantially in their native conformations, without significant degradation of the protein compared to, for example, DDM, one of the mildest known classical detergents.

Definitions

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

The phrase "one or more" is readily understood by one of skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the molecular level, for example, to bring about a chemical reaction or physical change, e.g., in a solution or other reaction mixture.

An "effective amount" generally means an amount which provides the desired effect.

The phrase "treating a protein" with a compound, detergent, or surfactant ("agent") refers to contacting the protein with the agent, and/or combining the protein with an effective amount of the agent under conditions that allow the agent to penetrate, integrate and/or disrupt a protein's environment in order to solubilize, isolate, and/or purify the protein. The conditions can be aqueous and additional reagents such as buffers and the like can be used. A combination of reagents may be employed in the treatment. The protein may be, for example, in a lipid bilayer or substantially isolated in solution.

The term "alkyl" refers to a branched or unbranched hydrocarbon having, for example, from 1 to 20 carbon atoms. Accordingly, the alkyl groups can be, for example, ($C_1$-$C_{20}$)

alkyl, $(C_2-C_{20})$alkyl, $(C_3-C_{20})$alkyl, $(C_4-C_{20})$alkyl, $(C_5-C_{20})$alkyl, $(C_8-C_{20})$alkyl, or any range of carbon atoms of an integer from 1 to 20. Examples include, but are not limited to, methyl, ethyl, 1-propyl, 2-propyl, 1-butyl, 2-methyl-1-propyl, 2-butyl, 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted with 1, 2, 3, 4, 5, 6, 7, 8, 9, or 10 substituents. For example, a substituted alkyl group can be a haloalkyl group, e.g., an alkyl group substituted with one or more halo groups as described below for the term substituted. In some embodiments, the alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., alkylene), according to the context of its usage. Additionally, the alkyl group can be optionally interrupted, as described below for the term interrupted.

As used herein, when a group or moiety can be substituted, the term "substituted" indicates that one or more (e.g., 1, 2, 3, 4, 5, or 6; in some embodiments 1, 2, or 3; and in other embodiments 1 or 2) hydrogens on the "substituted" group can be replaced with one or more of a selection of recited groups or with a suitable group known to those of skill in the art (e.g., one or more of the groups recited below), provided that the indicated atom's normal valency is not exceeded, and that the substitution results in a stable compound. Suitable substituents of a substituted group can include one or more of alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, difluoromethyl, acetylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano. Additionally, the suitable substituent groups can include, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heteroaryl, heterocycle, a protecting group or prodrug moiety. As would be readily understood by one skilled in the art, when a substituent is keto (=O) or thioxo (=S), or the like, then two hydrogen atoms on the substituted atom are replaced.

The term "interrupted" indicates that another group is inserted between two adjacent carbon atoms (and the hydrogen atoms to which they are attached (e.g., methyl (CH$_3$), methylene (CH$_2$) or methine (CH))) of a particular carbon chain being referred to in the expression using the term "interrupted", provided that each of the indicated atoms' normal valency is not exceeded and the interruption results in a stable compound. Suitable groups that can interrupt a carbon chain include, e.g., one or more non-peroxide oxy (—O—), thio (—S—), imino (—N(H)—), methylene dioxy (—OCH$_2$O—), carbonyl (—C(=O)—), carboxy (—C(=O)O—), carbonyldioxy (—OC(=O)O—), carboxylato (—OC(=O)—), imine (C=NH), sulfinyl (SO) or sulfonyl (SO$_2$) groups, or a combination thereof. Alkyl groups can be interrupted by one or more (e.g., 1, 2, 3, 4, 5, or about 6) of the aforementioned suitable groups. The site of interruption can also be between a carbon atom of an alkyl group and a carbon atom to which the alkyl group is attached.

The term "alkenyl" refers to a monoradical branched or unbranched partially unsaturated hydrocarbon chain (i.e. a carbon-carbon, sp$^2$ double bond). In one embodiment, an alkenyl group can have from 2 to 10 carbon atoms, or 2 to 6 carbon atoms. In another embodiment, the alkenyl group has from 2 to 4 carbon atoms. Examples include, but are not limited to, ethylene or vinyl, allyl, cyclopentenyl, 5-hexenyl, and the like. The alkenyl can be unsubstituted or substituted.

The term "alkynyl" refers to a monoradical branched or unbranched hydrocarbon chain, having a point of complete unsaturation (i.e. a carbon-carbon, sp triple bond). In one embodiment, the alkynyl group can have from 2 to 10 carbon atoms, or 2 to 6 carbon atoms. In another embodiment, the alkynyl group can have from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "cycloalkyl" refers to cyclic alkyl groups of from 3 to about 10 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like. The cycloalkyl can be unsubstituted or substituted. The cycloalkyl group can be monovalent or divalent, and can be optionally substituted as described above for alkyl groups. The cycloalkyl group can optionally include one or more cites of unsaturation, for example, the cycloalkyl group can include one or more carbon-carbon double bonds, such as, for example, cyclohexene, 1,3-cyclohexadiene, 1,4-cyclohexadiene, and the like. The cycloalkyl group can be a carbocycle, which refers to a saturated or partially unsaturated ring having 3 to 8 carbon atoms as a monocycle, 7 to 12 carbon atoms as a bicycle, and up to about 20 carbon atoms as a polycycle. Monocyclic carbocycles typically have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, or 1-cyclohex-3-enyl. The carbocycle can be optionally substituted as described above for alkyl groups.

The term "cycloalkyl alkyl" refers to an alkyl group that terminates in a cycloalkyl group. Examples include cyclopropylmethyl and cyclohexylethyl.

The term "aryl alkyl" refers to an alkyl group that terminates in an aryl group. Examples include benzyl and phenylethyl.

The term "alkoxy" refers to the group alkyl-O—, where alkyl is as defined herein. In one embodiment, alkoxy groups include, e.g., methoxy, ethoxy, n-propoxy, iso-propoxy, n-butoxy, tert-butoxy, sec-butoxy, n-pentoxy, n-hexyloxy, 1,2-dimethylbutoxy, and the like. The alkoxy can be unsubstituted or substituted.

As used herein, "aryl" refers to an aromatic hydrocarbon group derived from the removal of one hydrogen atom from a single carbon atom of a parent aromatic ring system. The radical can be at a saturated or unsaturated carbon atom of the parent ring system. The aryl group can have 6-18 carbon atoms, 6-14 carbon atoms, or 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described above for alkyl groups. For example, an aryl group can be substituted with one or more substituents (as described above) to provide various substituted aryls, such as pentafluorophenyl or para-trifluoromethylphenyl, and the like.

The term "halo" refers to the groups fluoro, chloro, bromo, and iodo. Similarly, the term "halogen" refers to fluorine, chlorine, bromine, and iodine.

As to any of the above groups, which contain one or more substituents, it is understood, of course, that such groups do not contain any substitution or substitution patterns that are sterically impractical and/or synthetically non-feasible. In addition, the compounds of this invention include all stereochemical isomers arising from the substitution of these compounds, including diasteriomers.

The term "saccharide" refers to a six carbon sugar or a dimer thereof, including amino sugars such as glucamine or gluconic acid derivatives (e.g., —$CH_2(CHOH)_4CH_2OH$ and —$C(=O)(CHOH)_4CH_2OH$, respectively). Six carbon sugars and dimers thereof can be referred to as monosaccharides or disaccharides, respectively. A saccharide group is a type of polar group ("$P^1$ or $P^2$"), which can be a substituent of another group, formula, or molecule. For example, a hydrogen or hydroxyl group can be removed from the polar group and replaced with a bond to another group, formula, or molecule. The polar group typically includes the anomeric oxygen of the parent saccharide when the group is shown as directly attached to a formula. The saccharide can be a monosaccharide such as such as allose, altrose, glucose, mannose, gulose, idose, galactose, or talose, a disaccharide such as maltose, galactose, or sucrose, or an amino or amide derivative thereof. The saccharide groups can also be in pyranose form, furanose form, or linear form.

Specific values listed below for radicals, substituents, and ranges, are for illustration only; they do not exclude other defined values or other values within defined ranges for radicals and substituents.

Amphiphiles and their Preparation.

Compounds of the formulas described herein can be prepared from readily available starting materials, such as dimethyl or diethyl malonate. One example of a preparation of an amphiphile of the invention is illustrated below in Scheme A.

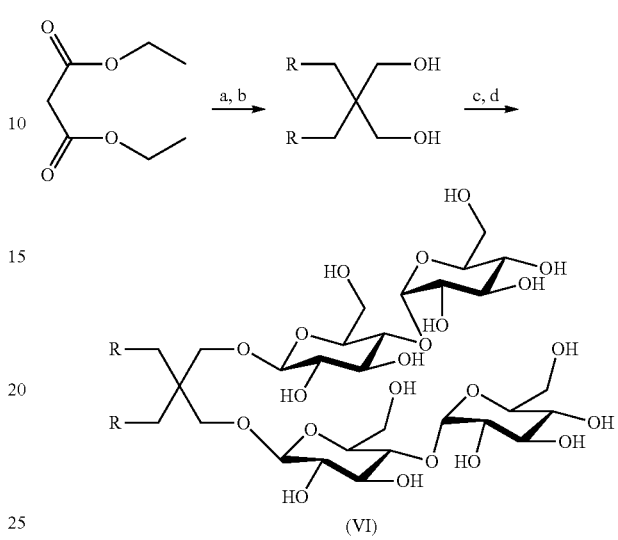

Scheme A. Preparation of Disaccharide Amphiphiles a) R-I, NaH, THF, 0° C.; b) LiAlH$_4$, THF, 0° C .→ 25° C.; c) perbenzoylated maltosyl bromide, AgOTf, CH$_2$Cl$_2$, -40° C. → 0° C.; d) NaOMe, MeOH, 25° C.; where R is, for example, (C$_4$-C$_{20}$)alkyl, (C$_5$-C$_{20}$)cycloalkyl, (C$_3$-C$_{20}$)cycloalkyl(C$_1$-C$_{20}$)alkyl, (C$_6$-C$_{10}$)aryl, (C$_6$-C$_{10}$)aryl(C$_1$-C$_{20}$)alkyl.

The approach provides significant flexibility, as would be readily recognized by one skilled in the art. For example, any number of R groups can be employed to provide a variety of non-polar tail groups. Also, different tail groups can be prepared, for example by sequentially adding different electrophiles (R groups) to the malonate nucleophile. The iodide of the group R-I can also be replaced with other suitable leaving groups, such as bromo, chloro, tosyl, or mesyl groups.

After reduction of the diester to a diol, a variety of saccharide groups can be attached. The perbenzoylated maltosyl groups are shown merely as one embodiment. Other protected monosaccharides and disaccharides can be used, with any suitable functionality at the anomeric position of the sugar.

Other amphiphiles, such as zwitterionic amphiphiles, can be prepared from readily available starting materials using standard synthetic transformations. Suitable transformations are illustrated in Schemes B, C, and D below.

Scheme B. Preparation of Zwitterionic Amphiphiles

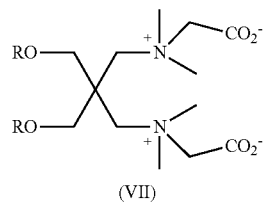

(VII)

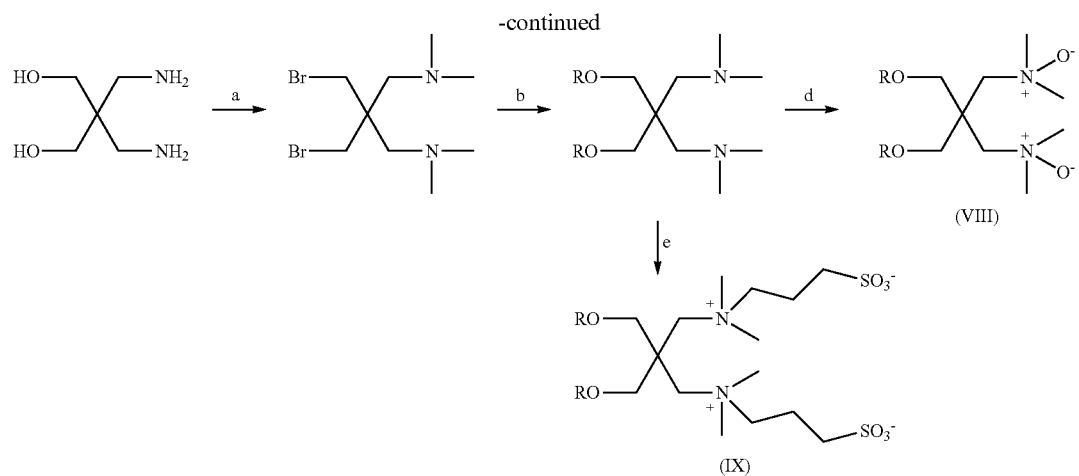

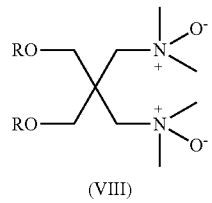

a) (CHO)$_n$, NaBH$_4$, MeOH, then CBr$_4$, Ph$_3$P, pyridine, CH$_2$Cl$_2$; b) ROH, NaH, DMF, 120° C.; c) sodium bromoacetate, Na$_2$CO$_3$; d) m-CPBA, CHCl$_3$; e) 1,3-propane sultone, DMF; where each R can independently be R$^1$, as defined for Formula I. The group RO— can be R$^1$—X— as defined for Formula I by conversion of a hydroxyl or bromo group to a suitable intermediate or R$^1$-X- group using standard synthetic transformations.

Scheme C. Preparation of Zwitterionic Amphiphiles

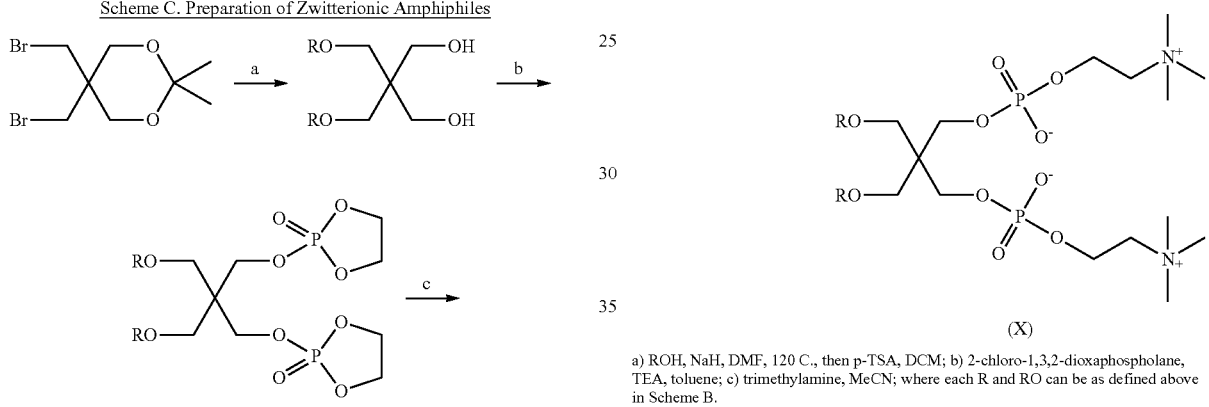

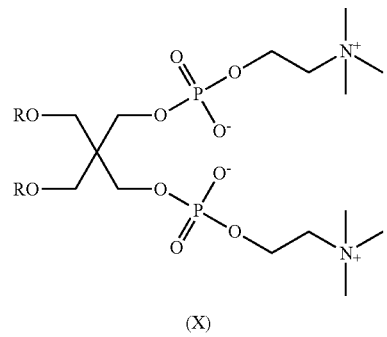

a) ROH, NaH, DMF, 120 C., then p-TSA, DCM; b) 2-chloro-1,3,2-dioxaphospholane, TEA, toluene; c) trimethylamine, MeCN; where each R and RO can be as defined above in Scheme B.

Scheme D. Preparation of Zwitterionic Amphiphiles

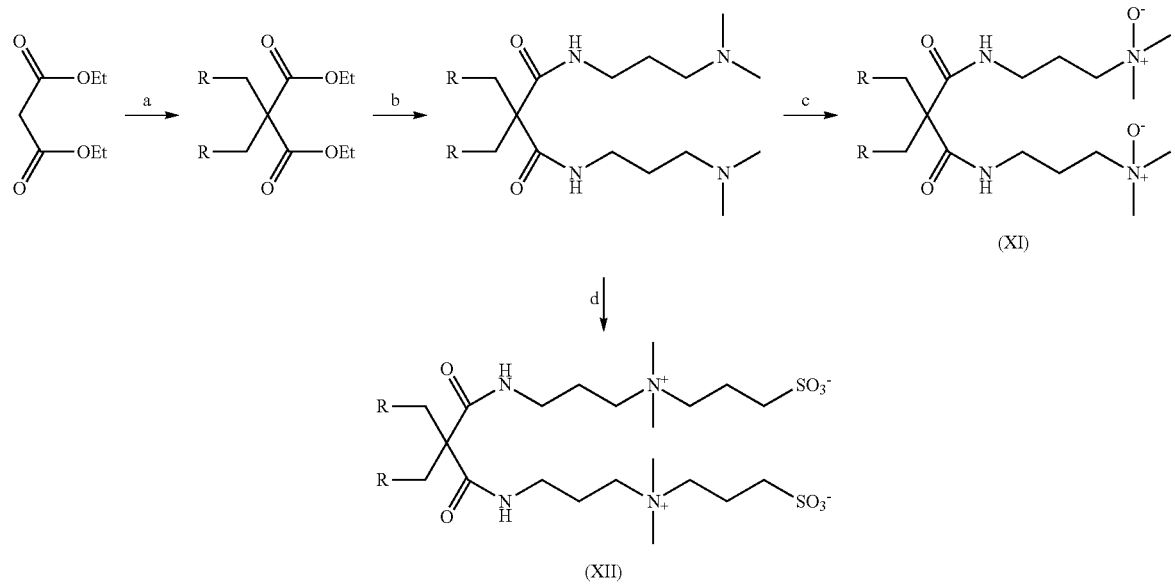

a) RI, NaH, THF; b) 3-dimethylaminopropyldiamine, DMF; c) m-CPBA, CHCl$_3$; d) 1,3-propane sultone, DMF; where each R can be as defined above in Scheme B.

Standard synthetic transformations known to those skilled in the art are described by, for example, Greg T. Hermanson in *Bioconjugate Techniques* (Academic Press, San Diego, Calif. (1996)); T. W. Greene in *Protecting Groups In Organic Synthesis* (Wiley: New York, Third Edition, 1999, and references cited therein); D. Voet in *Biochemistry* (Wiley: New York, 1990); L. Stryer in *Biochemistry* (3rd Ed., W.H. Freeman and Co.: New York, 1975); J. March in *Advanced Organic Chemistry, Reactions, Mechanisms and Structure* (2nd Ed., McGraw Hill: New York, 1977); and F. Carey and R. Sundberg in *Advanced Organic Chemistry, Part B: Reactions and Synthesis* (2nd Ed., Plenum: New York, 1977; and references cited therein).

GNG amphiphiles (compounds of Formulas I, II, or III wherein the saccharides are monosaccharides) may form small protein-detergent complexes when used to treat a membrane protein in an aqueous medium. The GNGs were found to be as effective as OG and LDAO detergents, and more effective than DDM for integral membrane protein solubilization. The GNGs were also milder than OG and LDAO for integral membrane protein stabilization, and were comparable to DDM in under several reaction conditions. Accordingly, the GNGs are believed to be useful for the solubilization and stabilization of relatively robust IMPs such as bacteriorhodopsin (bR).

In many instances, MNGs form comparable or smaller sized protein detergent complexes than DDM. MNGs are significantly more effective than DDM at maintaining the native state of IMPs under various standard reaction conditions. MNGs were found to be as effective as DDM for IMP solubilization, and are believed to be effective for the stabilization of fragile IMPs such as the *R. capsulatus* superassembly, and for the crystallization of fragile IMPs, which include the majority of unresolved IMPs to date.

Specific amphiphiles that can be prepared using the methods described above include the following GNG amphiphiles, MNG amphiphiles, and MPA amphiphiles illustrated below in Schemes E, F, and G. Examples include, for example, the compounds of Formulas XIII-XIX:

Scheme E. GNG Amphiphiles

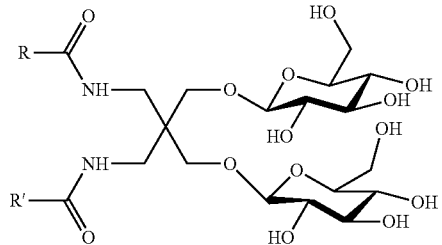

(XIII)

GNG-2: R = R' = n-C$_6$H$_{13}$
GNG-3: R = R' = 4-tert-butylphenyl
GNG-4: R = R' = cyclopentyl
GNG-5: R = R' = cyclohexyl

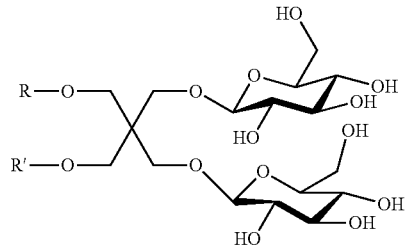

(XIV)

GNG-6: R = R' = n-C$_6$H$_{13}$
GNG-7: R = R' = n-C$_7$H$_{15}$
GNG-8: R = R' = 4-tert-butylphenyl
GNG-10: R = R' = Cyclohexyl
GNG-14: R = R' = n-C$_5$H$_{11}$

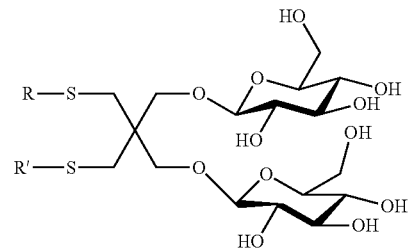

(XV)

GNG-1: R = R' = n-cyclohexyl
GNG-11: R = R' = 2-phenyl-ethyl

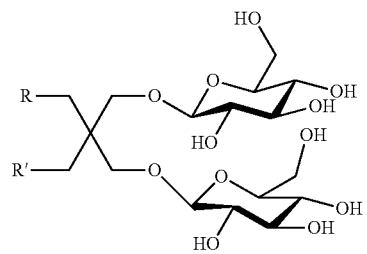

(XVI)

GNG-9: R = R' = n-C$_6$H$_{13}$
GNG-12: R = R' = n-C$_5$H$_{11}$
GNG-13: R = R' = n-C$_4$H$_9$

Scheme F. MNG Amphiphiles

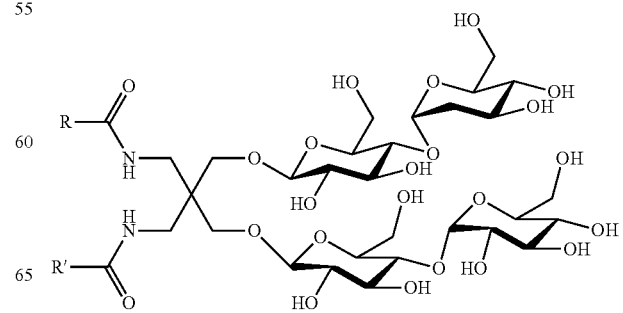

(XVII)

-continued

MNG-1: R = R' = n-C$_{10}$H$_{21}$
MNG-9: R = R' = 3-cyclohexylpropyl
MNG-10: R = R' = 4-cyclohexylbutyl
MNG-11: R = R' = norbornylmethyl
MNG-12: R = R' = adamantyl
MNG-13: R = R' = n-C$_9$H$_{19}$
MNG-21: R = dicyclohexylmethyl, R' = n-C$_7$H$_{15}$
MNG-22: R = dicyclohexylmethyl, R' = n-C$_8$H$_{17}$
MNG-23: R = R' = 3,5-Bis(trifluoromethyl)-phenylmethyl
MNG-24: R = R' = 3,5-Bis(trifluoromethyl)-phenylethyl
MNG-25: R = R' = 3,5-difluopheylmethyl
MNG-26: R = R' = 4-tert-butyl-cyclohexyl
MNG-27: R = R' = n-C$_{11}$H$_{23}$
MNG-29: R = R' = 2-cyclohexylethyl
MNG-15: R = n-C$_{13}$H$_{27}$, R' = n-C$_7$H$_{15}$
MNG-16: R = n-C$_{15}$H$_{31}$, R' = n-C$_5$H$_{11}$
MNG-17: R = n-C$_{12}$H$_{25}$, R' = n-C$_8$H$_{17}$
MNG-18: R = n-C$_{14}$H$_{29}$, R' = n-C$_6$H$_{13}$
MNG-19: R = 4-cyclohexylbutyl, R' = n-C$_7$H$_{15}$
MNG-20: R = R' = n-C$_8$H$_{17}$ (XVIII)

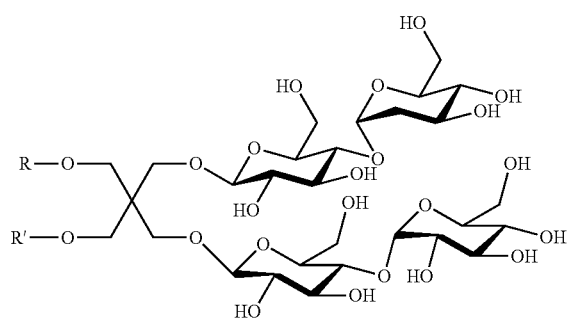

-continued

MNG-6: R = R' = n-C$_{10}$H$_{21}$
MNG-7: R = R' = 2-cyclohexylethyl
MNG-8: R = R' = 3-cyclohexylpropyl
MNG-30: R = R' = n-C$_9$H$_{19}$
MNG-31: R = R' = n-C$_8$H$_{17}$
MNG-32: R = R' = 6-undecyl
MNG-33: R = R' = 5-nonanyl
MNG-34: R = R' = n-C$_7$H$_{15}$ (XIX)

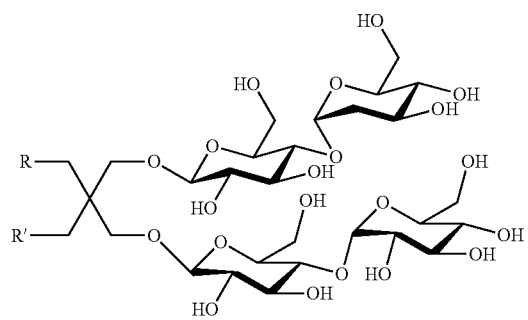

MNG-4: R = R' = n-C$_{10}$H$_{21}$
MNG-14: R = R' = n-C$_9$H$_{19}$
MNG-28: R = R' = n-C$_8$H$_{17}$
MNG-34: R = R' = n-C$_7$H$_{15}$
MNG-35: R = R' = cyclohexylmethyl
MNG-36: R = R' = 2-cyclohexylethyl
MNG-38: R = R' = n-C$_6$H$_{13}$ Scheme G. Specific MNG and MPA Amphiphiles

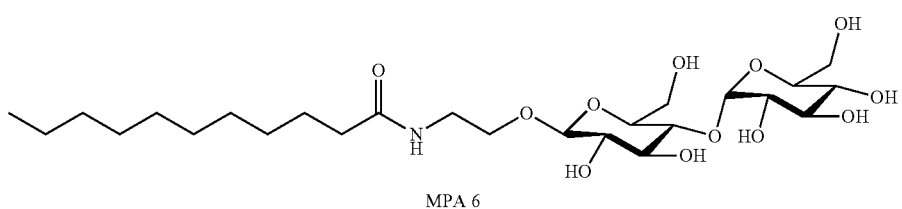

MPA 6

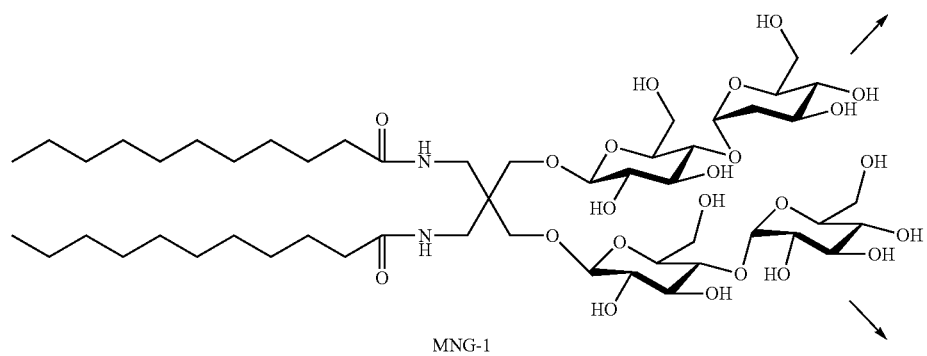

MNG-1

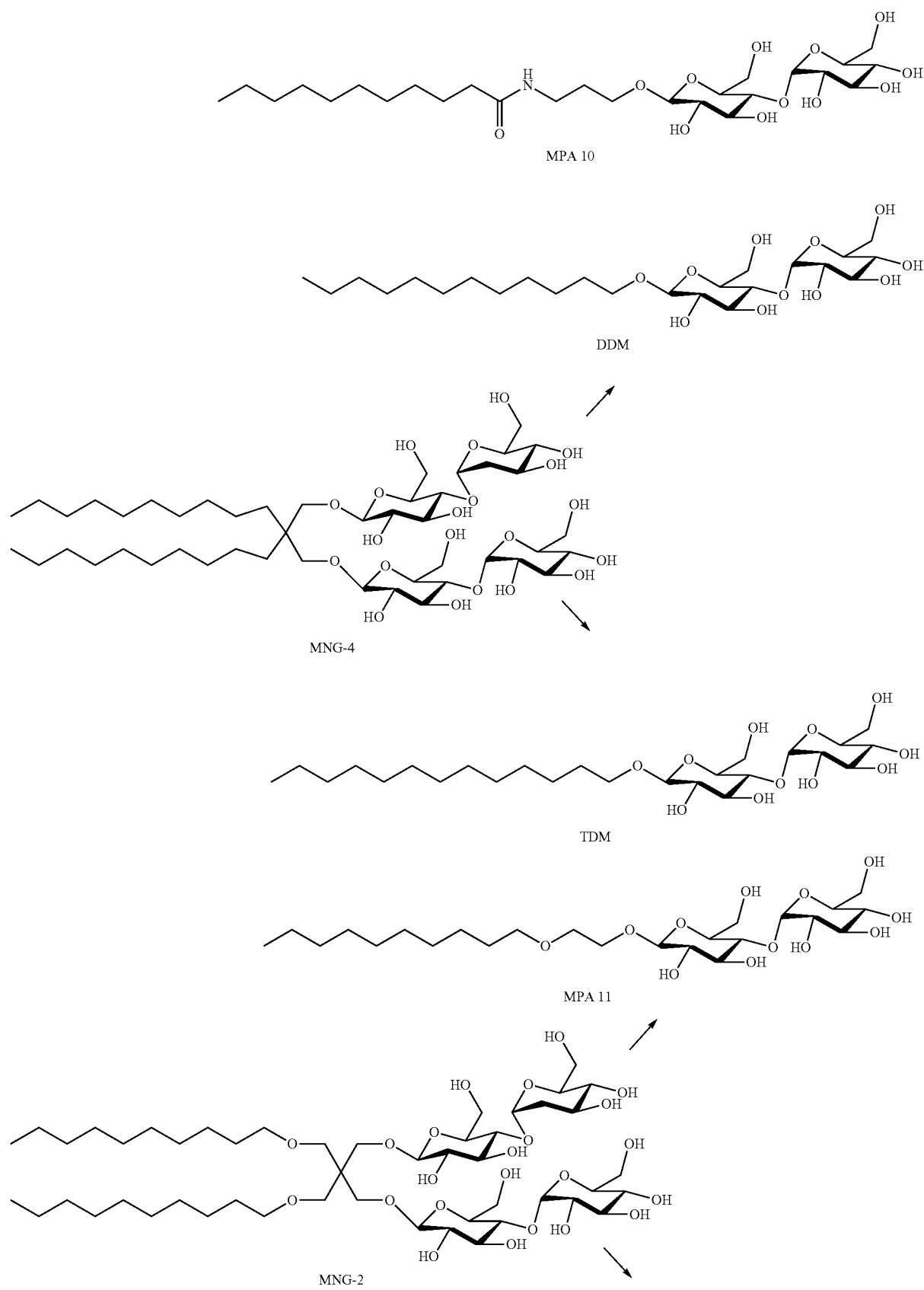

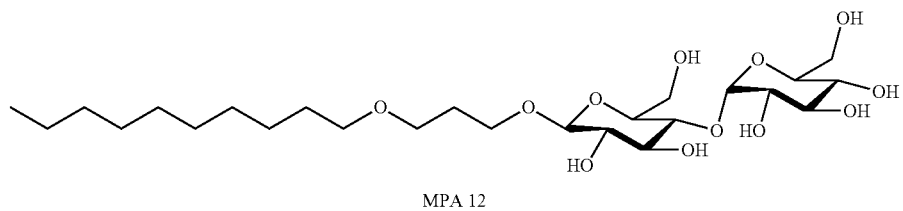

MPA 12

Solubilization Assays.

Light harvesting (LH) and reaction center (RC) complexes from photosynthetic bacteria (for example, *R. capsulatus*) are highly suitable for use in solubilization assays. These complexes, normally embedded in the bacterial membrane, are highly pigmented and several outcomes from an assay are possible, including no degradation, partial degradation or complete degradation upon solubilization, or no solubilization. Thus, graded comparative evaluations could be obtained for a set of candidates such as the carbohydrate-based amphiphiles described herein. In the engineered strain of *R. capsulatus* employed, the photosynthetic unit was comprised of a very labile LHI complex and a more resilient RC complex. An ideal amphiphile will extract the intact LHI-RC superassembly from a bacterial membrane preparation and maintain the natural interactions among the components. Amphiphiles with a more disruptive effect will dissociate and denature LHI, leaving only intact RC, and even harsher amphiphiles will cause RC degradation. Each of these various outcomes can be assessed unambiguously via optical spectroscopy.

Compound Characterization and Methods.

The Critical Micelle Concentrations (CMCs) of compounds of the invention can be determined by standard techniques known to those of skill in the art. For example, CMCs of the carbohydrate-based amphiphiles described herein can be determined by monitoring uptake of a fluorescent dye (e.g., a dye such as 1,6-diphenylhexatriene) with increasing detergent concentration, monitored by fluorescence spectroscopy.

When using the compounds of the invention for solubilization, isolation, purification, stabilization, crystallization, and/or structural determination of membrane proteins, they can be used alone, or in combination with commercially available detergents, such as CHAPS and/or CHAPSO, or other known detergents, such as those described in U.S. Pat. No. 6,172,262 (McQuade et al.) and by Hjelmeland in *Methods of Enzymology*, Vol. 124, page 135-164, which are incorporated herein by reference.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of Carbohydrate-Based Amphiphiles

Carbohydrate-based amphiphiles, such the amphiphiles illustrated in above in Schemes E, F, and G, can be prepared according to the steps outlined in Schemes 1-4 below. The synthesis of MNG amphiphiles are specifically described, however other amphiphiles, such as GNGs, can be prepared using analogous procedures and the corresponding glycosylhalide precursors.

General Procedure for Glycosylation Reactions. Glycosulation reactions were performed according to a literature method (Ashton et al., *Chem. Eur. J.* 2, 1115-1128 (1996)) with slight modification. A mixture of alcohol derivative, AgOTf (2.4 equiv.), 2,4,6-collidine (1.8 equiv.) in anhydrous $CH_2Cl_2$ (40 mL) was stirred at −45° C. A solution of perbenzoylated maltosylbromide (2.4 equiv.) in $CH_2Cl_2$ (40 mL) was added dropwise over 0.5 hours to this suspension. Stirring was continued for 0.5 hours at −45° C., and then the reaction mixture was allowed to warm to 0° C. and left stirring for 1.5 hours. After completion of reaction (as determined by TLC), pyridine was added to the reaction mixture, and it was diluted with $CH_2Cl_2$ (40 mL) before being filtered over celite. The filtrate was washed successively with a 1 M aqueous $Na_2S_2O_3$ solution (40 mL), a 0.1 M aqueous HCl solution (40 mL), and brine (2×40 mL). Then the organic layer was dried with anhydrous $Na_2SO_4$ and the solvents were removed by rotary evaporation. The residue was purified by silica gel column chromatography (EtOAc/hexane) providing the desired product as a glassy solid.

General Procedure for the de-O-benzoylations under Zemplén's conditions. The O-benzoylated compounds were dissolved in MeOH and then treated with the required amount of a methanolic solution of 0.5 M NaOMe such that the final concentration of NaOMe was 0.05 M. The reaction mixture was left stirring for 6 hours at room temperature, and then neutralized with Amberlite IR-120 ($H^+$ form) resin. The resin was removed by filtration and washed with MeOH and solvent was removed from the combined filtrate in vacuo. The residue was purified by silica gel column chromatography (MeOH/$CH_2Cl_2$). Further purification carried out by recrystallization using $CH_2Cl_2$/MeOH/diethyl ether afforded fully de-O-benzoylated product as a white solid. See Ashton et al., *Chem. Eur. J.* 2, 1115-1128 (1996) for generally related procedures.

Scheme 1. Preparation of MNG Amphiphiles

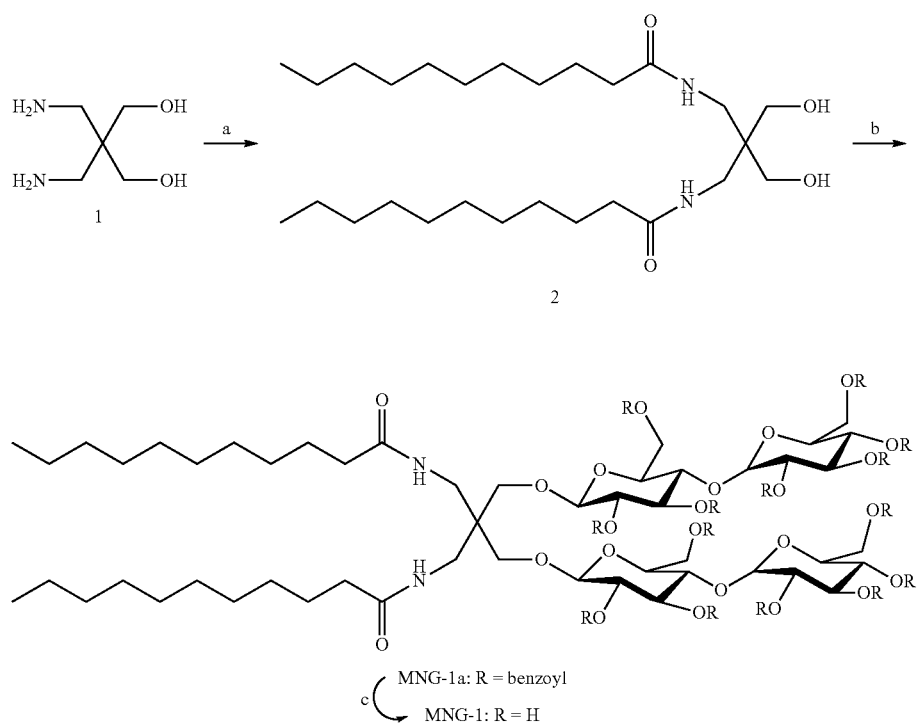

(a) undecanoic acid, EDC•HCl, HOBt, room temperature, 91%; (b) perbenzoylated maltosylbromide (2.4 equiv.), AgOTf, CH$_2$Cl$_2$, -45° C. → room temperature (~23° C.), 92%; (c) NaOMe, MeOH, room temperature, 95%.

Undecanoic acid (2,2-bis-hydroxymethyl-3-undecanoylamino-propyl)-amide (2). Compound 2 was synthesized according to Scheme 1 above. 2,2-Bis-aminomethyl-propane-1,3-diol (1)$^2$ (0.51 g, 3.8 mmol), undecanoic acid (1.42 g, 7.6 mmol), 1-hydroxybenzotriazole monohydrate (HOBt) (1.2 g, 9.1 mmol) was dissolved in anhydrous DMF (30 mL). Diol 1 can be prepared according to literature procedures (Virta et al., *J. Org. Chem.* 69, 2008-2016 (2004)). 1-(3-(Dimethylamino)propyl)-3-ethylcarbodiimide hydrochloride (EDC.HCl) (1.7 g, 0.91 mmol) was added in small portions at 0° C. and the resulting solution left stirring at room temperature for 20 hours. The solution was taken up with EtOAc (100 mL) and was washed successively with a 1 M aqueous NaHCO$_3$ solution (100 mL), a 0.1 M aqueous HCl solution (100 mL) and brine (2×100 mL). Then the organic layer was dried with anhydrous Na$_2$SO$_4$ and the solvent was removed by rotary evaporation. The reaction mixture was precipitated with ether (100 mL) and the resulting solid was collected and dried in vacuo to afford amide-containing diol 2 as a white solid (1.63 g, 91%). This product was used for next reaction without further purification.

Diol 2: $^1$H NMR (300 MHz, CDCl$_3$): δ 6.97 (t, J=6.8 Hz, 2H), 4.65 (t, J=6.6 Hz, 2H), 3.27 (d, J=7.0 Hz, 4H), 3.01 (d, J=7.0 Hz, 4H), 2.25 (t, J=7.4 Hz, 2H), 1.64 (quin, 4H), 1.30-1.23 (m, 28H), 1.38-1.21 (m, 6H), 0.88 (t, J=7.0 Hz, 6H); $^{13}$C NMR (75 MHz, CDCl$_3$): δ 176.1, 61.0, 46.6, 38.3, 36.9, 32.1, 29.8, 29.7, 29.5, 26.2, 22.9, 14.3; HRMS (ESI): calcd. for C$_{27}$H$_{54}$N$_2$O$_4$ [M]$^+$ 471.4157, found 471.4154.

MNG-1a was synthesized according to the general procedure for glycosylation.

$^1$H NMR (300 MHz, CDCl$_3$): δ 8.07 (d, J=8.4 Hz, 4H), 8.02-7.85 (m, 12H), 7.87 (d, J=8.4 Hz, 4H), 7.80 (d, J=8.4 Hz, 4H), 7.74 (d, J=8.4 Hz, 4H), 7.65-7.20 (m, 42H), 6.22-6.15 (m, 2H), 6.12 (t, J=10.0 Hz, 2H), 5.70 (d, J=4.1 Hz, 2H), 5.66 (t, J=10.0 Hz, 2H), 5.32 (t, J=9.4 Hz, 2H), 5.17 (dd, J=10.0, 3.5 Hz, 2H), 5.06 (dd, J=10.0, 8.0 Hz, 2H), 4.75 (d, J=10.0 Hz, 2H), 4.57 (dd, J=12.7, 3.2 Hz, 2H), 4.40-4.27 (m, 5H), 4.18 (dd, J=13.1, 4.4 Hz, 2H), 3.53 (d, J=9.6 Hz, 2H), 3.39 (m, 2H), 3.21 (d, J=8.0 Hz, 2H), 3.06 (m, 4H), 2.91 (dd, J=13.6, 3.0 Hz, 2H), 2.26 (t, J=7.5 Hz, 4H), 1.6 (br s, 4H), 1.35-1.15 (br s, 28H), 0.86 (t, J=6.9 Hz, 6H); $^{13}$C NMR (75 MHz, CDCl$_3$): δ 174.1, 166.2, 166.0, 165.9, 165.6, 165.4, 165.2, 165.1, 134.3, 133.8, 133.6, 133.5, 133.4, 133.3, 130.2, 130.1, 129.9, 129.8, 129.7, 129.5, 129.4, 129.2, 129.1, 129.0, 128.9, 128.8, 128.6, 128.5, 101.3, 95.9, 74.3, 72.8, 72.1, 71.4, 69.9, 69.3, 69.1, 62.7, 42.2, 42.0, 36.6, 32.0, 29.8, 29.7, 29.5, 26.0, 22.9, 14.3; MS (MALDI-TOF): calcd. for C$_{149}$H$_{150}$N$_2$O$_{38}$Na [M+Na]$^+$ 2597.9759, found 2597.9653.

MNG-1 was synthesized according to the general procedure for de-O-benzoylation. $^1$H NMR (300 MHz, CD$_3$OD): δ 5.20 (d, J=3.8 Hz, 2H), 4.34 (d, J=7.9 Hz, 2H), 3.96-3.80 (m, 8H), 3.73-3.63 (m, 9H), 3.60-3.39 (m, 10H), 3.38-3.22 (m, 7H), 2.27 (t, J=6.6 Hz, 4H), 1.65 (br t, 4H), 1.42-1.25 (br s, 28H), 0.93 (t, J=6.8 Hz, 6H); $^{13}$C NMR (75 MHz, CD$_3$OD): δ 177.1, 104.8, 103.1, 81.4, 77.9, 76.8, 75.2, 74.9, 74.8, 74.3, 71.7, 71.3, 62.9, 62.2, 45.9, 41.0, 37.5, 33.2, 30.9, 30.8, 30.6, 30.5, 27.2, 23.9, 14.6; HRMS (ESI): calcd. for C$_{51}$H$_{94}$N$_2$O$_{24}$Na [M+Na]$^+$ 1141.6089, found 1141.6071.

Scheme 2.

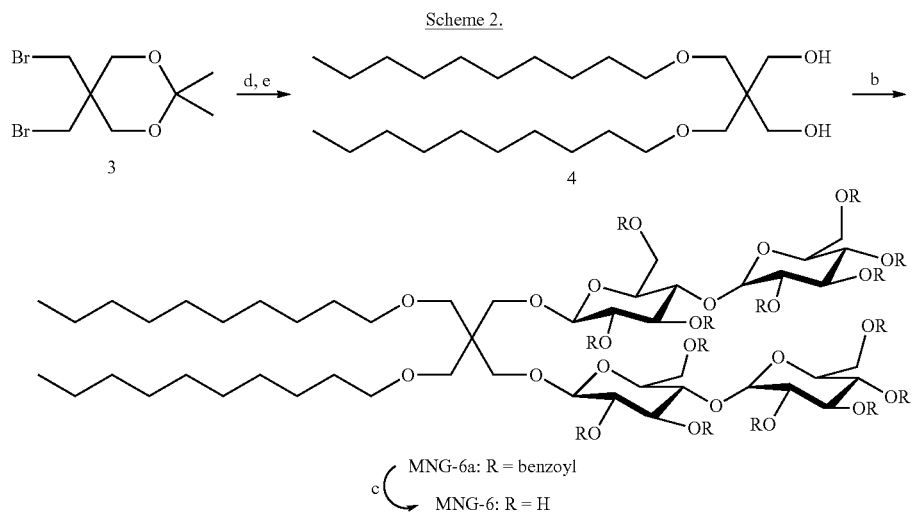

(d) decanol, NaH, DMF, 120° C.; (e) p-TSA, MeOH, room temperature, 92% (in two steps); (b) perbenzoylated maltosylbromide (2.4 equiv.) AgOTf, CH$_2$Cl$_2$, -45° C. → room temperature, 93%; (c) NaOMe, MeOH, room temperature, 96%.

2,2-Bis-decyloxymethyl-propane-1,3-diol (4). Compound 4 was synthesized according to Scheme 2 above. To a solution of decanol (3.3 g, 17 mmol) in DMF (40 mL) was added NaH (0.69 g, 0.17 mmol, 60%) at 0° C. The mixture was stirred at room temperature under N$_2$ atmosphere for 0.5 hours. After addition of 5,5-bis-bromomethyl-2,2-dimethyl-[1,3]dioxane (3)$^3$ (1.3 g, 4.3 mmol), the reaction mixture was warmed to 120° C. and stirred further for 15 hours. Dioxane 3 can be prepared according to the literature procedures of Nishizono et al., N., *Tetrahedron* 63, 11622-11625 (2007). After cooling to room temperature, the reaction was quenched with ice-cold H$_2$O (100 mL) and extracted with ether (3×80 mL). The combined organic layer washed with brine (2×100 mL), dried with anhydrous Na$_2$SO$_4$ and then concentrated by rotary evaporation. To the residue dissolved in 1:1 mixture of CH$_2$Cl$_2$ and MeOH (120 mL) was added p-toluenesulfonic acid (p-TSA) monohydrate (300 mg) and left stirring at room temperature for 2 hours. After the neutralization of the reaction mixture with a saturated aqueous NaHCO$_3$ solution, the volume of solvent was reduced by rotary evaporation. The residue was partitioned between CH$_2$Cl$_2$ and water. The separated organic layer was washed with brine, dried with anhydrous Na$_2$SO$_4$, and then concentrated in vacuo. Flash column chromatography (EtOAc/hexane) affords ether-containing diol 4 as a white solid (1.89 g, 92% (two steps)).

Diol 4: $^1$H NMR (300 MHz, CDCl$_3$): δ 3.64 (d, J=6.4 Hz, 4H), 3.51 (s, 4H), 3.42 (t, J=6.3 Hz, 4H), 2.87 (t, J=6.3 Hz, 2H), 1.56 (quin, J=6.7 Hz, 4H), 1.26 (br s, 28H), 1.38-1.21 (m, 28H), 0.88 (t, J=6.8 Hz, 6H); $^{13}$C NMR (75 MHz, CDCl$_3$): δ 73.4, 72.3, 71.1, 65.7, 44.7, 32.1, 29.8, 29.7, 29.6, 29.5, 26.4, 22.9, 14.3; HRMS (ESI): calcd. for C$_{25}$H$_{52}$O$_4$Na [M+Na]$^+$ 439.3758, found 439.3778.

MNG-6a was synthesized according to the general procedure for glycosylation. $^1$H NMR (300 MHz, CDCl$_3$): δ 8.07 (d, J=8.4 Hz, 4H), 8.02-7.95 (m, 8H), 7.91 (d, J=8.4 Hz, 4H), 7.87 (d, J=8.4 Hz, 4H), 7.80 (d, J=8.4 Hz, 4H), 7.74 (d J=8.4 Hz, 4H), 7.65-7.20 (m, 42H), 6.12 (t, J=9.8 Hz, 2H), 5.68 (d, J=4.5 Hz, 2H), 5.65 (t, J=9.4 Hz, 2H), 5.40 (t, J=9.8 Hz, 2H), 5.22-5.10 (m, 4H), 4.65-4.55 (m, 4H), 4.38-4.13 (m, 8H), 3.70 (d, J=9.2 Hz, 2H), 3.46 (d, J=8.0 Hz, 2H), 3.35-3.15 (m, 8H), 2.97 (t, J=9.4 Hz, 4H), 1.40 (br s, 4H), 1.33-1.12 (br s, 30H), 0.87 (t, J=7.0 Hz, 6H); $^{13}$C NMR (75 MHz, CDCl$_3$): δ 166.3, 166.0, 165.9, 165.7, 165.2, 165.0, 133.9, 133.6, 133.5, 133.4, 133.3, 130.3, 130.2, 130.1, 130.0, 129.9, 129.8, 129.7, 129.6, 129.5, 129.3, 129.2, 129.1, 129.0, 128.9, 128.8, 128.7, 128.6, 128.5, 128.4, 101.1, 95.9, 74.8, 72.4, 72.3, 71.7, 71.5, 69.9, 69.2, 69.1, 68.9, 68.6, 63.5, 62.7, 45.0, 32.1, 29.8, 29.7, 29.5, 26.2, 22.9, 14.3; MS (MALDI-TOF): calcd. for C$_{147}$H$_{148}$O$_{38}$Na [M+Na]$^+$ 2543.9541, found 2543.9468.

MNG-6 was synthesized according to the general procedure for de-O-benzoylation. $^1$H NMR (300 MHz, CD$_3$OD): δ 5.19 (d, J=3.8 Hz, 2H), 4.36 (d, J=7.9 Hz, 2H), 3.98-3.80 (m, 8H), 3.77-3.67 (m, 12H), 3.55-3.23 (m, 20H), 1.58 (br m, 4H), 1.45-1.30 (br s, 28H), 0.94 (t, J=6.8 Hz, 6H); $^{13}$C NMR (75 MHz, CD$_3$OD): δ 105.2, 103.1, 81.5, 78.0, 76.7, 75.2, 75.0, 74.9, 74.3, 72.8, 71.6, 62.9, 46.7, 33.2, 31.0, 30.9, 30.8, 30.7, 27.6, 23.9, 14.6; HRMS (ESI): calcd. for C$_{49}$H$_{92}$O$_{24}$Na [M+Na]$^+$ 1087.5871, found 1087.5876.

Scheme 3.

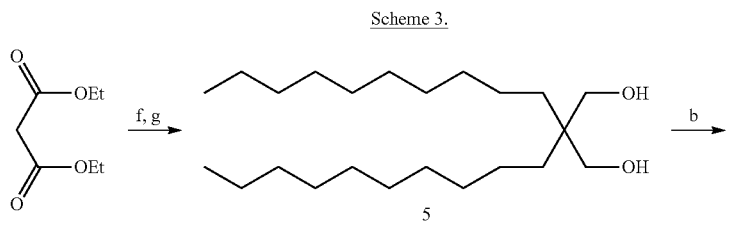

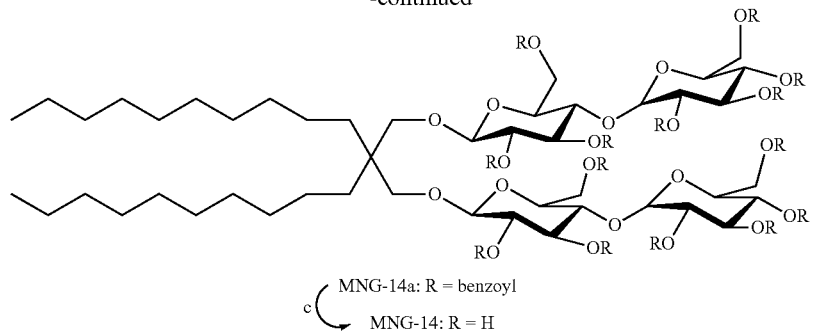

MNG-14a: R = benzoyl
MNG-14: R = H (f) NaH, decyl iodide, THF, room temperature; (g) LiAlH$_4$, THF, room temperature, 93% (in two steps); (b) perbenzoylated maltosylbromide (2.4 equiv.), AgOTf, 2,4,6-collidine, CH$_2$Cl$_2$, -45° C. → room temperature, 90%; (c) NaOMe, MeOH, room temperature, 94%.

2,2-Bis-decyl-propane-1,3-diol (5). This compound was synthesized according to a literature method (Kim et al., Tetrahedron Lett. 36, 5147-5150 (1995)) with slight modification, as illustrated in Scheme 3 above. To a solution of diethyl malonate (1.04 mL, 6.9 mmol) in THF (40 mL) was added dropwise a solution of NaH (0.82 g, 21 mmol) in THF at 0° C. and left stirring for 20 minutes. After addition of iododecane (3.8 mL, 18 mmol), the reaction mixture was stirred at room temperature for 24 hours, quenched by adding ice-cold saturated NH$_4$Cl (100 mL) and then extracted with diethyl ether (2×50 mL). The organic layer was washed with brine and dried with anhydrous Na$_2$SO$_4$. After complete evaporation of solvent, LiAlH$_4$ (0.52 g, 14.0 mmol) was added slowly to the residue dissolved in THF (50 mL) at 0° C. The mixture was stirred at room temperature for 4 hours, quenched with MeOH, water, a 1 N aqueous HCl solution successively at 0° C. and then extracted with diethyl ether (2×50 mL). The combined organic layer was washed with brine and dried with anhydrous Na$_2$SO$_4$. The residue was purified by silica gel column chromatography (EtOAc/hexane) providing alkyl-containing diol 5 as a white solid (2.3 g, 93% (two steps)).

Diol 5: $^1$H NMR (300 MHz, CDCl$_3$): δ 3.55 (s, 4H), 2.55 (s, 2H), 1.38-1.08 (m, 36H), 0.88 (t, J=6.8 Hz, 6H); $^{13}$C NMR (75 MHz, CDCl$_3$): δ 69.6, 41.2, 32.1, 31.0, 30.8, 29.9, 29.8, 29.6, 23.1, 22.9, 14.3; HRMS (ESI): calcd. for C$_{23}$H$_{48}$O$_2$Na [M+Na]$^+$ 379.3547, found 379.3546.

MNG-14a was synthesized according to the general procedure for glycosylation. $^1$H NMR (300 MHz, CDCl$_3$): δ 8.05 (d, J=8.4 Hz, 4H), 8.02-7.95 (m, 8H), 7.92 (d, J=8.4 Hz, 4H), 7.86 (d, J=8.4 Hz, 4H), 7.86 (d, J=8.4 Hz, 4H), 7.80 (d, J=8.4 Hz, 4H), 7.75-7.18 (m, 42H), 6.12 (t, J=9.8 Hz, 2H), 5.68-5.58 (m, 4H), 5.34 (t, J=10.2 Hz, 2H), 5.18-5.06 (m, 4H), 4.68-4.52 (m, 4H), 4.38-4.16 (m, 8H), 3.32 (d, J=7.6 Hz, 2H), 2.94-2.86 (m, 2H), 2.70 (d, J=8.6 Hz, 2H), 1.35-0.98 (m, 34H), 0.87 (t, J=6.9 Hz, 6H); $^{13}$C NMR (75 MHz, CDCl$_3$): δ 166.3, 166.0, 165.7, 165.3, 165.2, 165.0, 133.9, 133.7, 133.6, 133.4, 133.3, 130.3, 130.1, 130.0, 129.9, 129.8, 129.7, 129.6, 129.4, 129.2, 129.0, 128.9, 128.8, 128.6, 128.5, 95.9, 74.5, 72.3, 72.2, 71.5, 69.2, 62.8, 40.4, 32.1, 30.6, 30.3, 29.9, 29.8, 29.7, 29.6, 22.9, 22.3, 14.3; MS (MALDI-TOF): calcd. for C$_{145}$H$_{144}$O$_{36}$Na [M+Na]$^+$ 2483.9330, found 2483.928.

MNG-14 was synthesized according to the general procedure for de-O-benzoylation. $^1$H NMR (300 MHz, CD$_3$OD): δ 5.18 (d, J=3.8 Hz, 2H), 4.39 (d, J=7.9 Hz, 2H), 3.98-3.78 (m, 4H), 3.77-3.60 (m, 6H), 3.58-3.23 (m, 20H), 1.58 (br m, 6H), 1.42-1.16 (br s, 34H), 0.93 (t, J=6.8 Hz, 6H); $^{13}$C NMR (75 MHz, CD$_3$OD): δ 105.1, 103.0, 78.0, 76.6, 74.9, 74.8, 71.6, 42.2, 33.2, 31.7, 30.9, 30.8, 30.6, 23.9, 14.6; HRMS (ESI): calcd. for C$_{47}$H$_{88}$O$_{22}$Na [M+Na]$^+$1027.5660, found 1027.5653.

MPA compounds can be prepared as illustrated below in Scheme 4.

Scheme 4.

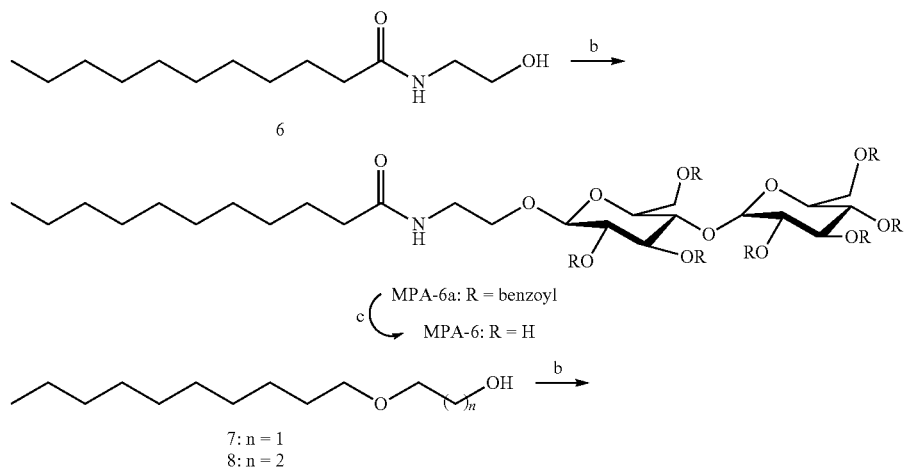

MPA-6a: R = benzoyl
MPA-6: R = H

7: n = 1
8: n = 2

-continued

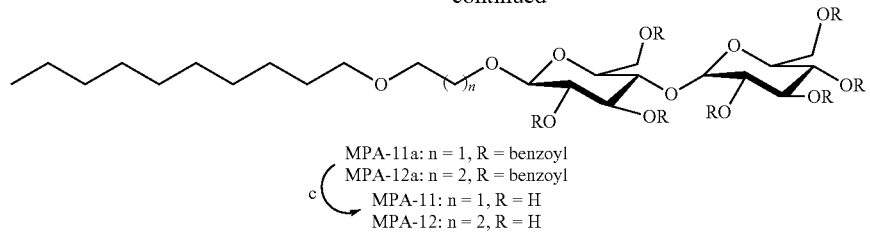

MPA-11a: n = 1, R = benzoyl
MPA-12a: n = 2, R = benzoyl
MPA-11: n = 1, R = H
MPA-12: n = 2, R = H (b) perbenzoylated maltosylbromide (2.4 equiv.), AgOTf, CH$_2$Cl$_2$, -45° C. → room temperature, 95% (MPA-6a), 94% (MPA-11a), 93% (MPA-12a);
(c) NaOMe, MeOH, room temperature, 96% (MPA-6), 95% (MPA-11 and MPA-12).

Example 2

Solubilization and Purification of *Rhodobacter capsulatus* Membrane Proteins

A protocol has been developed to enable researchers to evaluate and determine the efficacy of detergents for use in solubilizing membrane proteins. The resulting classification is generally applicable to a wide range of detergents, including the amphiphiles of the invention.

Detergents were tested with homogenized *Rhodobacter capsulatus* membranes containing photosynthetic protein superassemblies. The homogenate used (*Rhodobacter capsulatus* RC) is light sensitive therefore work should be carried out under low intensity light. Starting with protein complexes in their native lipid bilayer, two important detergent properties were tracked, allowing for a strength ranking to be assigned to any given detergent.

Amphiphile Screening and Stabilization.

Measurements. The starting material for the screening protocols and stability measurements included specialized photosynthetic membranes from an engineered strain of *Rhodobacter (R.) capsulatus*, U43[pUHTM86Bgl] (Kirmaier et. al. 2003. *Journal of Physical Chemistry B*. 106: 1799-1808), lacking the LHII light-harvesting complex. Membranes from this strain containing large quantities of the LHI-RC superassembly were isolated in advance, according to methods outlined by Laible and coworkers, and were flash frozen (Laible et al. 1998. *Biophysical Journal*. 74: 2623-2637). To begin the solubilization and purification process, frozen aliquots of *R. capsulatus* membranes were thawed, homogenized, and equilibrated to 32° C. for 30 minutes. Disruption of the lipid bilayer and solubilization of the membrane protein complexes commenced with the addition of the desired amphiphile (compound of the invention) at about 1 wt. % concentration.

The membrane samples were allowed to incubate with the amphiphile for 30 minutes at 32° C. The solubilized material was then separated from the membrane debris in an ultracentrifuge at 315,000×g at 4° C. for 30 minutes. The pellet, containing membrane protein complexes not removed from the lipid bilayer, was resuspended and homogenized with 1 mL of 10 mM Tris buffer (pH 7.8) and 100 mM NaCl. After a UV-Vis-nearIR absorption spectrum was recorded, the resuspended pellet was discarded. The supernatant from the spin was pipetted into a new microcentrifuge tube containing Ni-NTA resin (Qiagen, Inc.; Valencia, Calif.; pre-equilibriated and stored in an equal volume of buffer containing 10 mM Tris, pH 7.8 and 100 mM NaCl). The tubes were then incubated and inverted for 1 hour at 4° C. During this period, only the reaction center can be bound to the Ni-NTA resin because of the engineered hepta-histidine tag on the C-terminus of the M subunit (Goldsmith et al. 1996. *Biochimica et Biophysica Acta*. 1276: 171-175; Pokkuluri et al. 2002. *Biochemistry*. 41: 5998-6007; Kirmaier et al., 2003 *Chemical Physics*. 294: 305-318).

Once binding was complete, samples were loaded onto resin-retaining spin columns (e.g., emptied His Spin Trap™ columns; GE Healthcare). The columns were then inserted into a 2 mL microcentrifuge tube to retain the filtered solution during centrifugation. Samples were rinsed twice with 0.5 mL of amphiphile-containing binding 15 buffer (a 7.8 pH Tris solution containing the amphiphile used for solubilization at its CMC). Finally, protein was eluted into a fresh microcentrifuge tube with three 0.2 mL elution buffer aliquots (this buffer was identical to binding buffer with the addition of 1 M imidazole).

The *R. capsulatus* LHI-RC complexes extracted and purified by this procedure contain large numbers of cofactors that have absorptions at distinct wavelengths, and each component of the LHI-RC superassembly has a different inherent stability outside the lipid bilayer. The solubilization protocol outlined above therefore provides a multifaceted assessment of the efficacy of conventional detergents and novel amphiphiles. UV-Vis absorption spectroscopy data obtained at various stages of the protocol allow one to determine which protein components have degraded at these stages. The results reveal the relative potency of amphiphiles in disrupting a lipid bilayer and subsequently stabilizing the photosynthetic superassembly or subunits thereof. The disruption potential was measured as the yield of superassembly extracted during solubilization (or, alternatively and more precisely, as the absence of superassembly in the pellet from the spin following solubilization).

The stabilizing propensity was determined from the spectra of the purified protein. An amphiphile was judged to be mild and stabilizing if it allowed the purification of fully intact LHI-RC superassembly (dominant absorption band at 875 nm). An amphiphile was judged to be strong and destabilizing if it resulted in little or no purified protein with absorption in the near IR, or led to isolation of the intact RC (which is relatively robust) in the absence of LHI. In this latter case, the RC was often damaged, as indicated by a large absorption at 760 nm (released co-factors) or dominant absorption at 800 nm with a shoulder at 850 nm, which indicates that the functional RC remains but it has lost a lipid that is normally bound tightly when the RC resides in its native lipid bilayer (Wang et al., 1994. *Photosynthesis Research*. 42: 203-215). An amphiphile was judged to be of intermediate strength if it allowed for the purification of fully intact RC with damaged or missing LHI (dominant absorption at 800 nm with a shoulder at 875 nm; damaged LHI still bound to RC absorbs 20 at 760 nm).

Similar criteria and protocols were used to judge the ability of amphiphiles to maintain solubilized and purified superassembly for extended periods. In this case, UV Vis-nearIR spectra were recorded at regular intervals. The degradation of the material could be monitored with the $A_{875}/A_{680}$ absorbance ratio, which decreased with time and sample integrity as the dominant 875 nm absorption of intact LHI disappeared and a 680 nm band appeared, indicating the presence of unbound, oxidized cofactors.

Protein Solubilization and Purification Using Amphiphiles of the Invention.

Figure 2A:
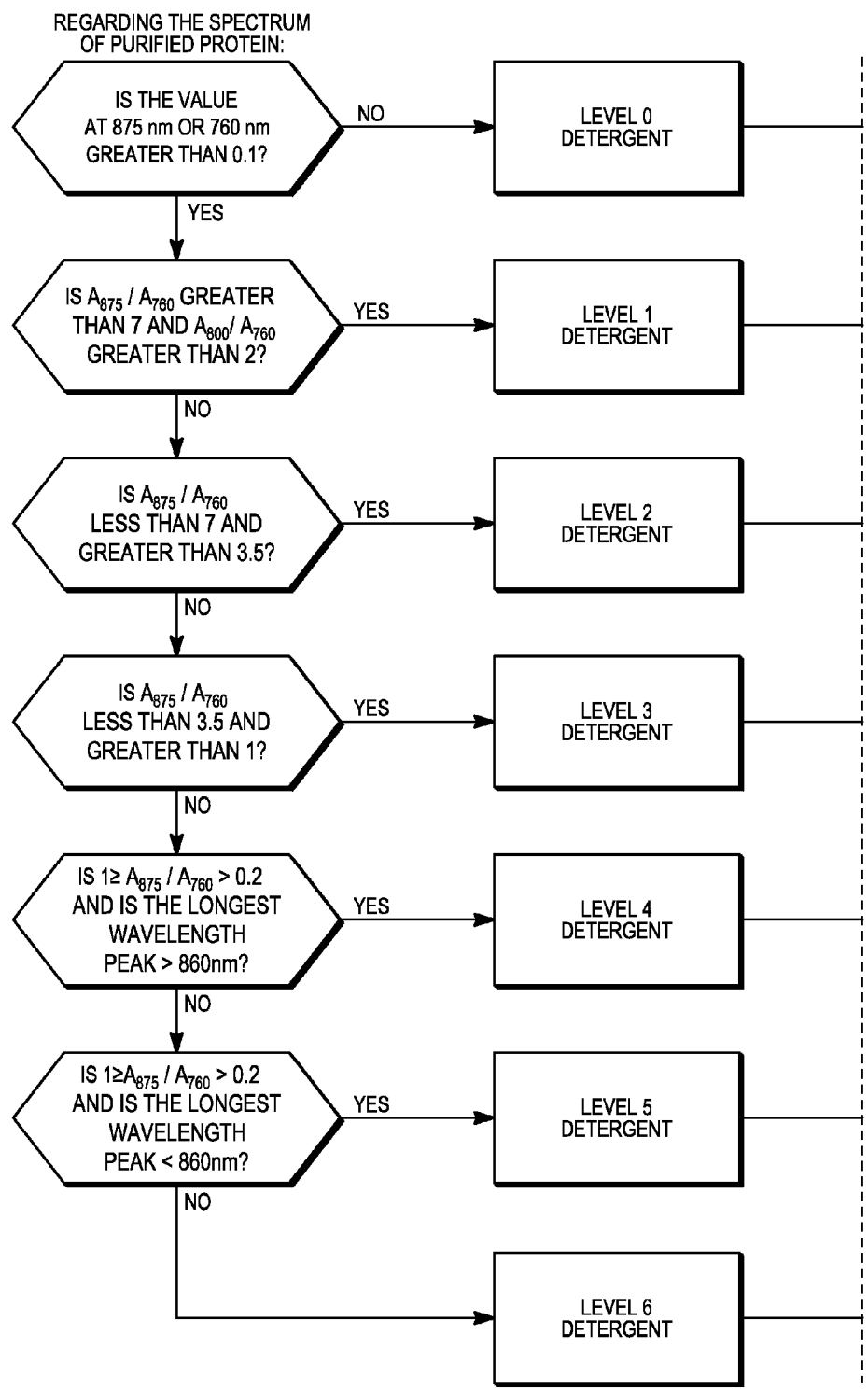
FIG. 2 illustrates a flow chart depicting a decision tree utilized for classification of amphiphilic compounds in the assay described in Example 2, according to an embodiment of the invention. Class determinations were based quantitatively on a specific absorbance ratio ($A_{875}/A_{760}$ and $A_{800}/A_{760}$). The ratio of a sample of completely folded and functional superassembly is >7.0 at $A_{875}/A_{760}$ and >2.0 at $A_{800}/A_{760}$; these ratios declines dramatically as the multi-subunit complex disassembles and denatures.
Figure 2B:
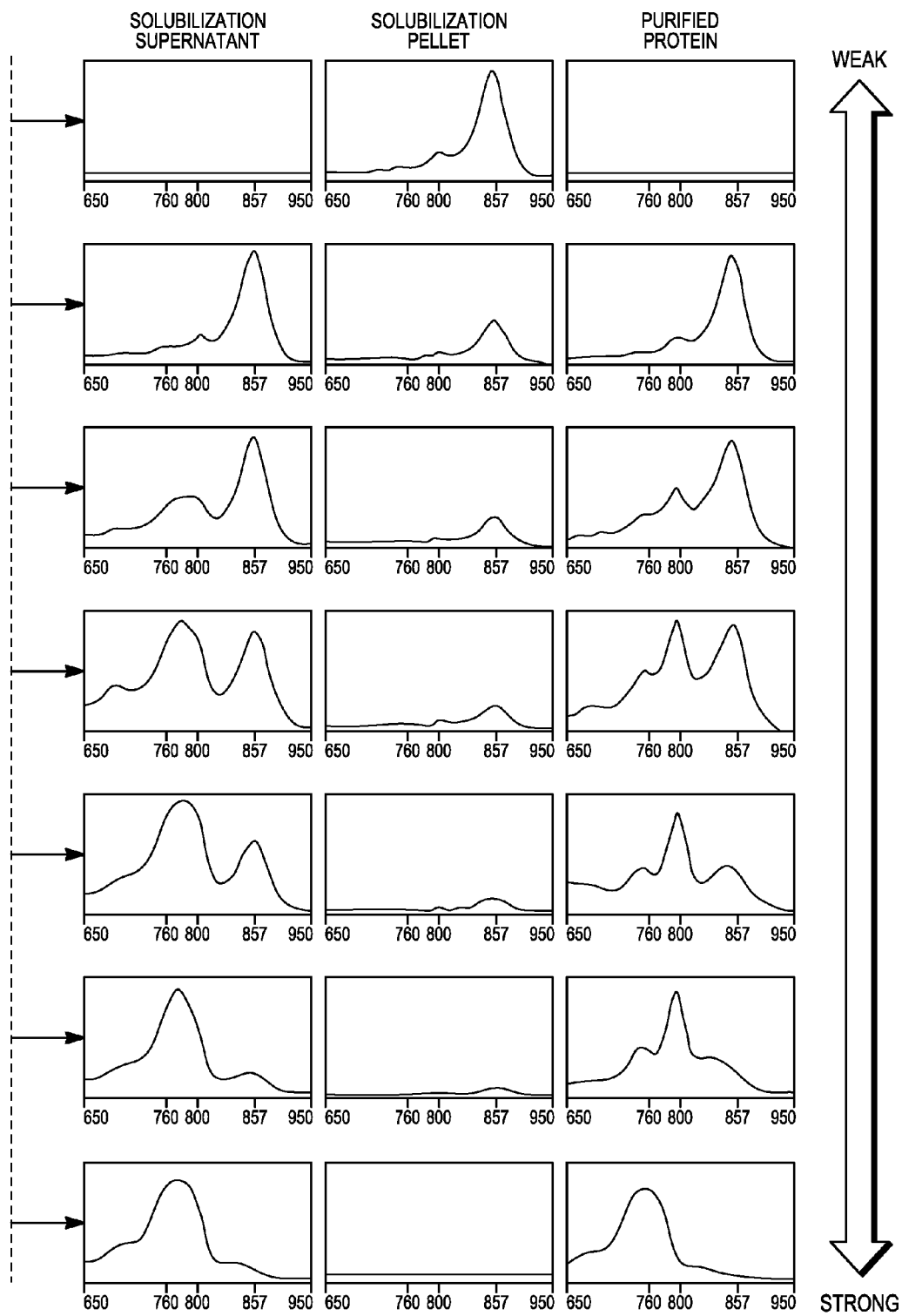

First, solubilization (illustrated in "STEP 1" of FIG. 1) denotes the ability of a surfactant to penetrate, integrate and disrupt a lipid bilayer. This ability is demonstrated by the intensity of the spectral absorption bands of the Solubilization Supernatant (SS) and the Solubilization Pellet (SP). Secondly, the ability of micelles of the test surfactant to stabilize a membrane protein outside of a lipid bilayer can be assayed. For the second type of rating (illustrated in "STEP 2" of FIG. 1), spectra of the Purified Protein (PP) are used. Thus, FIG. 1 provides a graphical depiction of the following detailed steps for protein solubilization and purification, and the procedure for assigning a level to a particular detergent is illustrated in the flowchart of FIG. 2.

Step 1: Solubilization

The following procedure can be used to evaluate solubilization properties of a detergent. The specific amounts of reagents, times, temperatures, and pH can be varied depending on various experimental factors such as the amount of homogenate available, the amount of detergent available, and the like, as would be readily understood by one skilled in the art. Solubilization Evaluation Procedure:

A) Thaw a 10 mL aliquot of *Rhodobacter capsulatus* RC homogenate ($OD_{875}$ 7.5). Although the membranes may be homogenized once prior to freezing, use a small volume glass tissue homogenizer to uniformly distribute the membrane suspension a second time after it has completely thawed. Equilibrate the homogenate to an appropriate temperature (32° C.) by inverting the entire sample in an Enviro-Genie® refrigerated incubator (or similar machine that allows inversions at a controlled temperature) for at least 30 minutes.

B) Divide the homogenate into 1 mL aliquots (to allow for ten possible screens for one tube of membrane stock) in microcentrifuge tubes. Add the detergent of interest at 10×CMC. Invert in the Enviro-Genie® refrigerated incubator for 30 minutes at 32° C. Use at least two controls (for example, LDAO and n-dodecyl-β-D-maltopyranoside) and one blank (no detergent) to ensure that data can be reliably evaluated.

C) Place the solubilized membrane suspension in a polycarbonate ultracentrifuge tube. Pellet the membrane debris in a tabletop ultracentrifuge at 315,000×g (for example, an Optima™ TLX tabletop ultracentrifuge; TLA 120.2 rotor; 85K rpm) for 30 minutes at 4° C.

D) Record a spectrum (from 650 nm to 950 nm) of the solubilized supernatant (SS), then reserve the supernatant for purification (STEP 2 below). Using a small glass homogenizer, resuspend the remaining pellet with 1 mL of buffer containing 10 mM Tris, pH 7.8 and 100 mM NaCl. Record a spectrum of the resuspended pellet (SP). Dilute to appropriately remain within the dynamic range of the spectrophotometer employed. The resuspended pellet can be disposed of after the spectrum has been recorded.

The 875 nm peak from the spectrum of the Solubilization Pellet of the blank (no detergent) is used to determine the percentage of complexes that were extracted from samples incubated with detergent. If the 875 nm peak of an experimental sample is at or above 50% of the blank peak, the detergent obtains an "S" rank to indicate the majority of the complexes were extracted after solubilization and reside in the Supernatant. Conversely, a detergent obtains the rank of a "P" if peaks are below 50% of the blank peak, indicating the detergent is too weak to effectively penetrate, integrate and disrupt the lipid bilayer, leaving the majority of the complexes within the Pellet.

Step 2: Purification

E) Transfer each SS from step "D" into fresh and separate microfuge tubes. Invert a stock of Ni-NTA resin (Qiagen, Inc.; Valencia, Calif.; prequilibriated and stored in an equal volume of buffer containing 10 mM Tris, pH 7.8 and 100 mM NaCl) until the beads are completely mixed throughout the storage solution. Then add 200 μL of the Ni-NTA resin to each tube containing SS (so that one obtains 100 μL of resin in the tube). Invert the microfuge tubes containing the SS+resin in an Enviro-Genie® refrigerated incubator (or equivalent) for 1 hour at 4° C. to allow ample time for the histidine-tagged complex to bind to the resin.

F) His-Spin Trap™ columns (GE Healthcare) can be used to purify the protein. These columns are pre-packaged with resin in place. Previous experiments indicated that the resin supplied with the His-Spin Trap™ columns does not bind proteins as well as the Ni-NTA Qiagen resin (necessitating the addition of the Qiagen resin in step "E"). These columns are used for the ease of washing and eluting the Ni-NTA resin, however the resin originally received with these columns is not used in this procedure. If a new His-Spin Trap™ column is being used, remove and discard the top cap and break off the bottom closure. Clean and rinse the column using water so that no resin remains.

Place the column in a 2 mL microcentrifuge tube to collect the liquid during centrifugation. Add 500-600 μL (when maximum column volume is 600 μL) of the SS to the column and centrifuge for 30 seconds at 70×g. Remove the flow-through and reserve it in a separate tube. Add any remaining SS and centrifuge again. Two spin cycles are typically required to centrifuge an entire sample. Combine all of unbound material. Although the flow-through from these spins is not used to determine detergent strength, spectra can be recorded to observe elements that did not bind to the column during purification. These spectrum profiles can also help determine if a particular detergent is interfering with affinity chromatography and is not allowing the histidine-tagged reaction center to properly bind to the nickel-charged resin. Once a spectrum of the unbound material has been recorded, it can be discarded.

G) Wash the column resin by adding 500 μL binding buffer (a 7.8 pH, 10 mM Tris solution containing 1×CMC of the detergent used for solubilization) to the column. Centrifuge for 30 seconds at 70×g. Repeat this step to wash the column a second time. If significant pigmentation is noticed in the column washes, record its spectrum. Otherwise, the eluent may be discarded.

H) Use a new 2 mL microcentrifuge tube for this step. Use of new tubes avoids contamination of the purified protein with any residual material that was rinsed off during the column wash. After the column is placed in a new 2 mL microcentrifuge tube, elute the target protein by subjecting the bound protein and resin to three separate aliquots of 200 μL of elution buffer (the binding buffer with the addition of 1 M imidazole). Centrifuge the column for 30 seconds at 70×g between each addition of elution buffer. If a stock Tris solution already at a pH of 7.8 is being used for the buffers, ensure that the pH of this solution is adjusted again to 7.8 after the addition of imidazole.

I) To facilitate spectroscopy, add 400 μL of binding buffer to the purified protein to adjust the volume of 1 mL. Record a spectrum of the purified protein. The reference is a solution containing 10 mM Tris, pH 7.8. From the spectrum of the purified protein, each detergent can be classified into one of six categories (weak to strong detergent) according to the flowchart in FIG. 2.

TABLE 1

CMC values and class evaluation for R. capsulatus superassembly.

| Detergent | M.W. | CMC (mM) | CMC (%) | Classification |
|---|---|---|---|---|
| GNG-1 | 656.8 | 2.1 | 0.13 | S1 |
| GNG-2 | 682.8 | 18 | 1.2 | S1 |
| GNG-3 | 778.9 | — | — | aggregation |
| GNG-4 | 650.7 | 72 | 4.7 | — |
| GNG-5 | 678.8 | — | — | Insoluble |
| GNG-6 | 628.7 | 1.55 | 0.08 | S1 |
| GNG-7 | 656.8 | 0.1 | 0.0092 | S1 |
| GNG-8 | 724.8 | — | — | aggregation |
| GNG-9 | 596.7 | 0.11 | 0.0066 | limited solubility |
| GNG-10 | 624.7 | 17 | 1.07 | S1 |
| GNG-11 | 700.9 | 0.82 | 0.06 | S1 |
| GNG-12 | 568.7 | 1.02 | 0.058 | S1 |
| GNG-13 | 540.6 | 9.64 | 0.373 | S1 |
| GNG-14 | 600.7 | 13.4 | 0.647 | S1 |
| MNG-1 | 1119.3 | 0.017 | 0.0019 | S1 |
| MNG-2 | 1195.4 | — | — | insoluble |
| MNG-3 | 1161.3 | — | — | aggregation |
| MNG-4 | 1033.2 | 0.0037 | 0.00038 | P1 |
| MNG-5 | — | — | — | — |
| MNG-6 | 1065.2 | 0.009 | 0.00096 | S1 |
| MNG-7 | 1033.2 | 0.043 | 0.00447 | S1 |
| MNG-9 | 1087.2 | 0.39 | 0.043 | P1 or S1 |
| MNG-10 | 1115.3 | 0.053 | 0.0059 | P1 or S1 |
| MNG-11 | 1055.1 | 12.9 | 1.4 | P1 or S1 |
| MNG-12 | 1107.2 | — | — | P1 or S1 |
| MNG-13 | 1091.2 | 0.043 | 0.0047 | P1 or S1 |
| MNG-14 | 1005.2 | 0.01 | 0.001 | S1 |
| MNG-15 | 1119.3 | 0.02 | 0.0022 | N.D. |
| MNG-16 | 1119.3 | 0.023 | 0.0026 | N.D. |
| MNG-17 | 1119.3 | 0.02 | 0.002 | N.D. |
| MNG-18 | 1119.3 | 0.024 | 0.0027 | N.D. |
| MNG-19 | 1075.2 | 0.18 | 0.0194 | N.D. |
| MNG-20 | 1063.2 | 0.3 | 0.0319 | P1 or S1 |
| MNG-21 | 1115.3 | 0.24 | 0.0268 | N.D. |
| MNG-22 | 1129.3 | 0.12 | 0.0136 | N.D. |
| MNG-23 | 1291 | 0.9 | 0.1162 | P1 or S1 |
| MNG-24 | 1319 | 0.84 | 0.1108 | P1 or S1 |
| MNG-25 | 1119 | 10 | 1.119 | P1 or S1 |
| MNG-26 | 1115.3 | 0.12 | 0.0134 | P1 or S1 |
| MNG-27 | 1147.3 | 0.008 | 0.0009 | P1 or S1 |
| MNG-28 | 977.1 | 0.018 | 0.0018 | P1 or S1 |
| MNG-30 | 1037.2 | 0.017 | 0.0018 | P1 or S1 |
| MNG-31 | 1009.1 | 0.034 | 0.0034 | P1 or S1 |
| MNG-33 | 1037.2 | 0.092 | 0.0095 | P1 or S1 |
| MNG-34 | 949.1 | 0.036 | 0.0034 | P1 or S1 |
| MNG-35 | 945.1 | 0.15 | 0.014 | P1 or S1 |
| MNG-36 | 973.1 | 0.058 | 0.0056 | P1 or S1 |

The column labeled Classification indicates whether the specific amphiphile successfully solubilized the majority of the protein into the supernatant (S) or if the protein remained in the pellet (P). Also, the detergent strength of the amphiphiles was determined as described above, with level 1 indicating the mildest detergent strength and level 6 indicating the strongest detergents. Generally, maltosides have fallen into levels 1 or 2, glucosides have fallen into levels 3 or 4, and N-oxides have fallen into level 6 in the case of classical detergents. N.D. indicates that the classification was not yet determined at the time the table was prepared.

Table 1 shows the efficacy of several amphiphiles of the invention. The lower CMC values indicate that less detergent is required for manipulating membrane proteins. Lower amounts of detergent can simplify characterization and analysis of the membrane proteins, indicating the value of the new detergents disclosed herein.

The detergent strength, determined according to the procedures outlined above, and illustrated in FIGS. 1 and 2, can be use to aid a determination of which amphiphile to select for manipulating different types of proteins. While mild detergents are suitable for manipulating certain membrane proteins, stronger detergents are sometimes necessary for others. Accordingly, the invention provides a range of amphiphiles for use with various types of membrane proteins, including integral membrane proteins and extrinsic membrane proteins, and the classification system described herein can aid in determining which amphiphile to select for commencing membrane protein analysis.

In some embodiments, a gain in stabilization efficacy can result in some loss in solubilization efficiency. More efficient amphiphiles interact more strongly with membrane proteins, resulting in harsher detergent properties. Stronger detergents are desirable for some applications but not for others, therefore new amphiphiles with a range of properties are needed to aid membrane protein research. Each specific amphiphile or class of amphiphiles may be highly effective for handling a specific type or class of membrane protein, and other specific amphiphiles or amphiphile classes may be highly suitable for various purposes, such as solubilization, isolation, purification, stabilization, crystallization, and/or structural determination of membrane proteins, depending on the desired technique to be performed.

Example 3

MNG Amphiphiles for Manipulating Membrane-Bound Proteins

Figure 3:
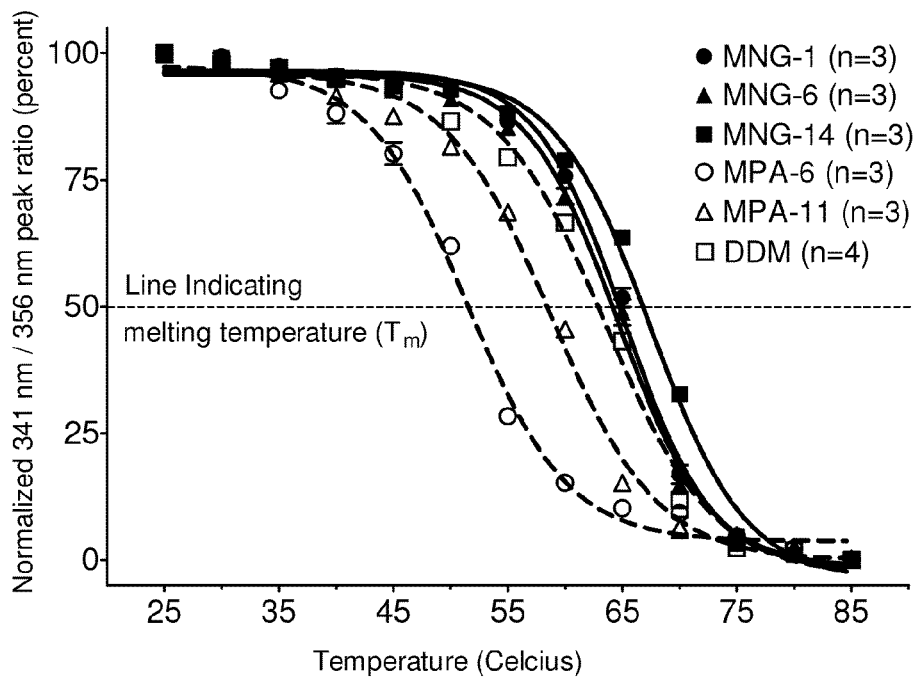
FIG. 3 illustrates the results of comparing MNGs to MPAs at 10×CMC for stabilization efficacy of $\beta_2$ adrenergic receptor-T4-lyosome fusion protein (β2AR-T4L), according to an embodiment of the invention.
Figure 4:
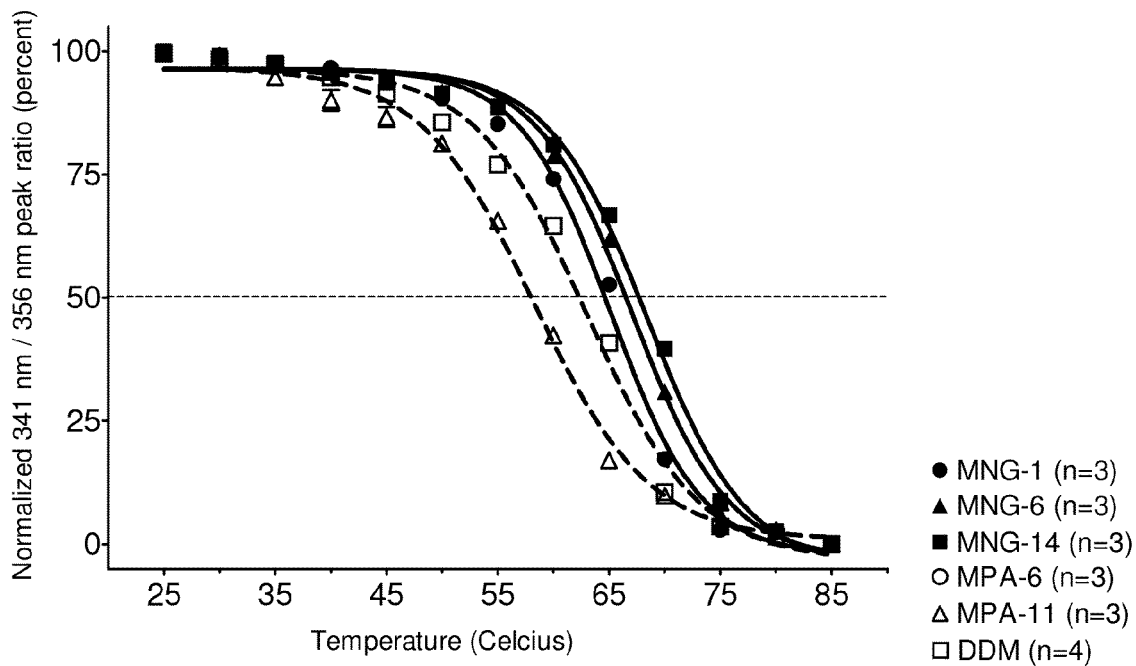
FIG. 4 illustrates the results of comparing MNGs to MPAs at 50×CMC for stabilization efficacy of β2AR-T4L, according to an embodiment of the invention. Similar to FIG. 3, the horizontal dotted line extending from 50% on the y-axis in FIG. 4 indicates the melting temperature ($T_m$).

The branched amphiphiles of the invention have shown to have several advantageous properties that match or surpass those of many known amphiphiles. The branched nature provide improved stabilization, attributable to the dual saccharide chains, and improved solubilization, attributable to the dual hydrophobic tail groups. FIGS. 3 and 4 show a comparative study showing normalized peak ratios (341 nm/356 nm) for six different amphiphiles (illustrated in Schemes F and G) from 25° C. to 85° C., at 10×CMC and 50×CMC for human $\beta_2$ adrenergic receptor-T4-lyosome fusion protein ($\beta$2AR-T4L). Table 2 shows a $T_m$ summary of MNGs and MPAs for $\beta$2AR-T4L.

TABLE 2

| | MNG results for β2AR-T4L | | | | | | |
|---|---|---|---|---|---|---|---|
| | 10 × CMC | | 50 × CMC | | 250 × CMC | | |
| | Tm | ΔTm | Tm | ΔTm | Tm | ΔTm | ΔTm |
| DDM‡ | 63.5 (n = 4)* | | 63.0 (n = 4) | | 62.2 (n = 4) | | |
| MPA-6 | 51.4 (n = 3)* | −12.1 | N.D. | N.D. | N.D. | N.D. | −12.1 |
| MPA-11 | 58.8 (n = 3)* | −4.7 | 58.3 (n = 3) | −4.7 | N.D. | N.D. | −4.7 |
| MNG-1 | 65.1 (n = 3)* | +1.6 | 65.1 (n = 3)* | +2.1 | N.D. | N.D. | +1.6 |

TABLE 2-continued

| | MNG results for β2AR-T4L | | | | | | |
|---|---|---|---|---|---|---|---|
| | 10 × CMC | | 50 × CMC | | 250 × CMC | | |
| | Tm | ΔTm | Tm | ΔTm | Tm | ΔTm | ΔTm |
| MNG-4 | 64.1 (n = 3) | +0.6 | 67.3 (n = 3)* | +4.3 | N.D. | N.D. | +3.8 |
| MNG-6 | 64.6 (n = 3) | +1.1 | 67.1 (n = 3)* | +4.1 | N.D. | N.D. | +3.6 |
| MNG-14 | 67.4 (n = 3) | +3.9 | 68.4 (n = 3)* | +5.4 | 66.8 (n = 3) | +4.6 | +4.9 |

‡ = 10 × CMC = 0.07% DDM.
* = Individual detergent concentration with highly favorable stabilizing effect on β2AR.

Each MNG had better micelle properties than any MPAs at 10 times CMC and 50 times CMC. The best $T_m$s of all MNGs were higher than those of MPAs at the concentrations investigated. MNG-14 showed the best overall properties for stabilizing β2AR-T4L, and all MNGs were more tolerant of CMC concentration in the stabilization of β2AR-T4L relative to MPAs.

Example 4

Crystals Prepared by a use of MGN Amphiphiles

Crystals of membrane proteins can be prepared by a processes involving single amphiphiles described herein, or using a combination of amphiphiles such as MNGs, as described below. The following two experiments demonstrate that MNG amphiphiles stabilize the β2-adrenal receptor (β$_2$AR) for lipidic cubic phase (LCP) crystallization, and that MNG-14 and MNG-28 enhance the function of purified M3 muscarinic receptor.

MNG stabilizes the β$_2$AR for lipidic cubic phase (LCP) crystallization. LCP methods have proven useful for crystallizing membrane proteins, including G protein-coupled receptors (GPCRs). However, the process of incorporating membrane proteins from a detergent solubilized state into LCP can lead to denaturation of the protein. Efforts to obtain crystals of the β$_2$AR bound to an agonist using the LCP method were unsuccessful, because an agonist bound β$_2$AR in dodecylmaltoside (DDM) is not sufficiently stable to survive the transition to LCP. However, when dodecylmaltodide was exchanged for MNG-14 before incorporation into LCP, diffraction quality crystals were obtained.

Figure 5:
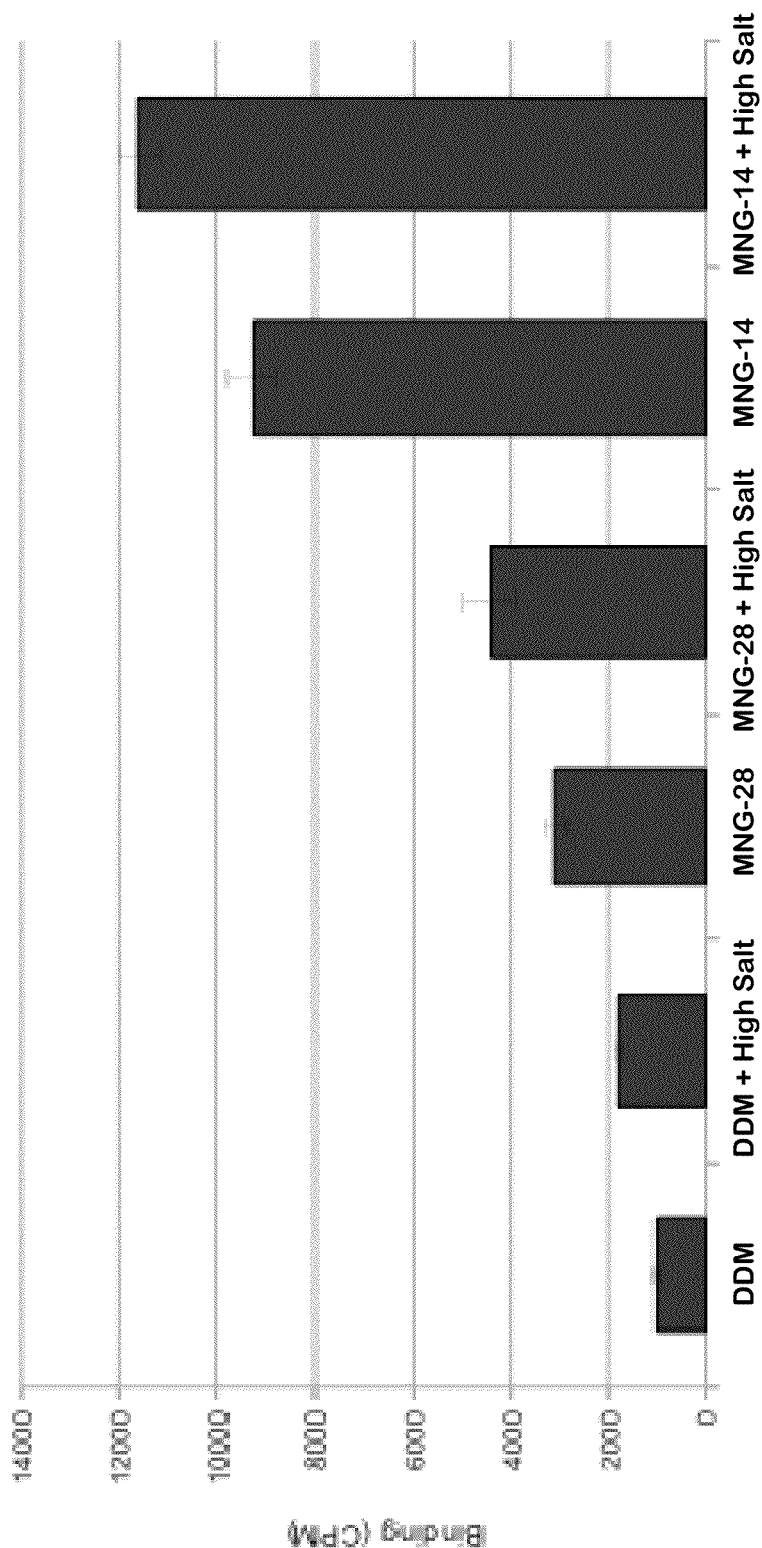
FIG. 5 illustrates binding of antagonists in different amphiphiles/detergents, where binding (counts per minute (CPM)) is three-fold greater upon the addition of MNG-28, and nine-fold higher upon the addition of MNG-14, compared to the use of DDM alone.

MNG-14 and MNG-28 enhance the function of purified M3 muscarinic receptor. M3 muscarinic receptor purified from baculovirus infected insect cells using the detergent dodecylmaltoside exhibits little specific binding to the muscarinic antagonist [$^3$H]N-methylscopolamine ([$^3$H]NMS). For FIG. 5, the samples (DDM, MNG-28, and MNG-14) were combined with HEPES pH 7.5 buffer in a 100 mM NaCl solution. The samples "+High Salt" had a final NaCl concentration of 500 mM. Binding (counts per minute (CPM)) is three-fold greater upon the addition of MNG-28, and nine-fold higher upon the addition of MNG-14, as illustrated in FIG. 5. Therefore, the amphiphilic compounds described herein, such as the MNG amphiphiles, provide new options for enhancing the function and analysis of various isolated and/or purified proteins and receptors.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of Formula I for manipulating membrane proteins:

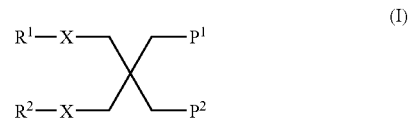

(I)

wherein
R$^1$ is (C$_4$-C$_{20}$)alkyl;
R$^2$ is (C$_4$-C$_{20}$)alkyl;
each X is CH$_2$ or a direct bond;
P$^1$ is a disaccharide; and
P$^2$ is a disaccharide.

2. The compound of claim 1 that is

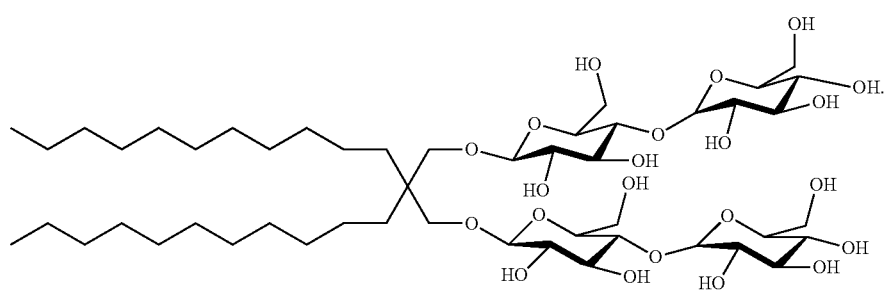

MNG-4

3. The compound of claim 1 that is
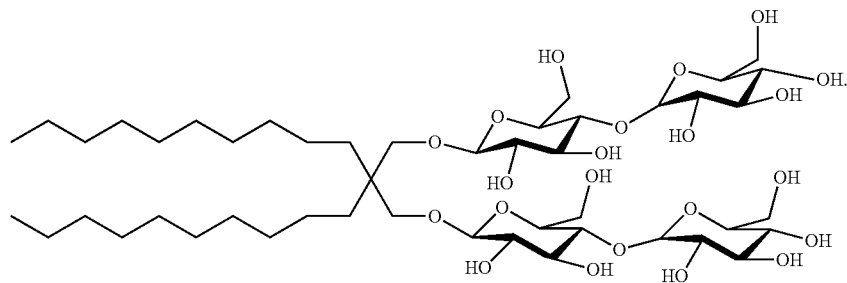
MNG-14
4. The compound of claim 1 that is
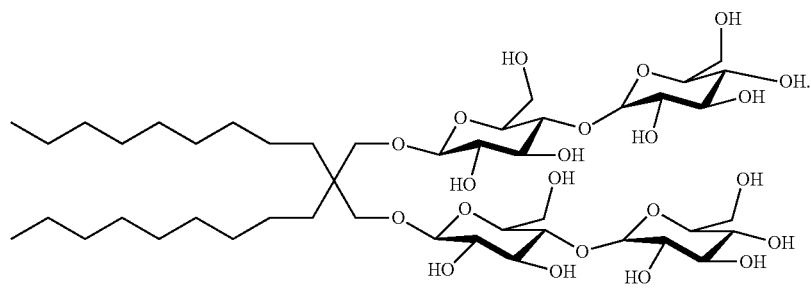
MNG-28
5. The compound of claim 1 that is
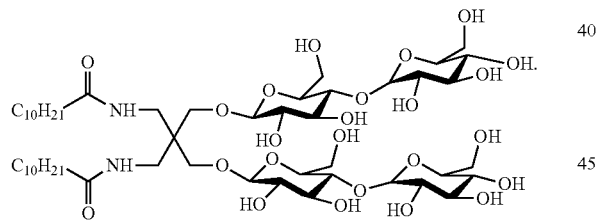
MNG-1
6. A compound selected from the group consisting of
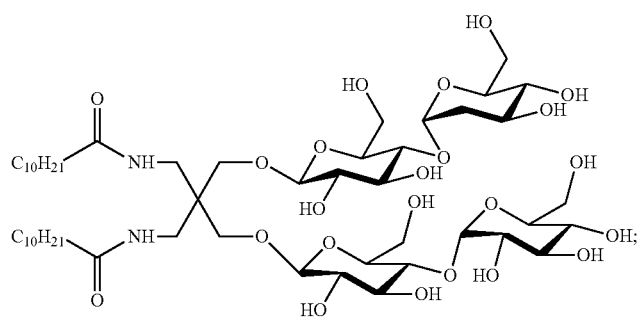
MNG-1

-continued
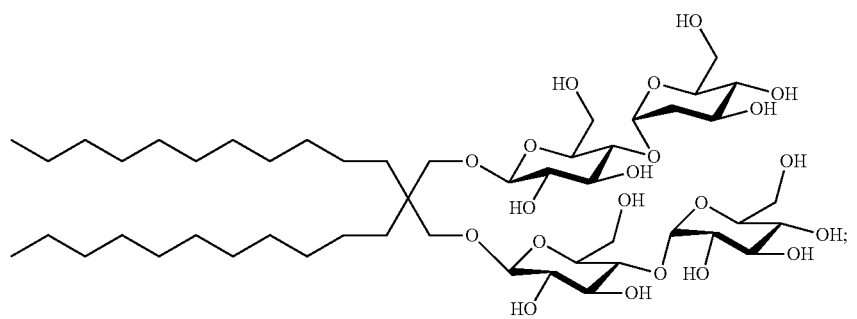
MNG-4
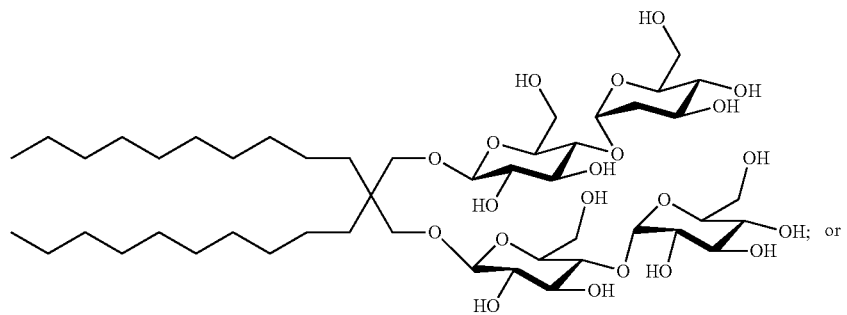
MNG-14
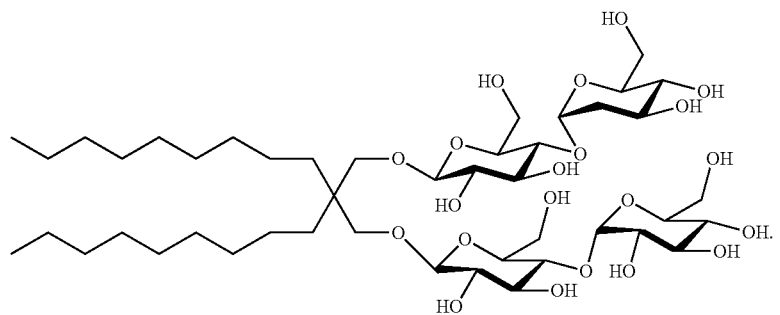
MNG-28
* * * * *